(12) United States Patent
Gutierrez et al.

(10) Patent No.: US 8,096,996 B2
(45) Date of Patent: Jan. 17, 2012

(54) ROD REDUCER

(75) Inventors: Robert Gutierrez, Huntington Beach, CA (US); Shawn Tebbe, Oceanside, CA (US); Moti Altarac, Irvine, CA (US); Stanley Kyle Hayes, Mission Viejo, CA (US); Joey Camia Reglos, Lake Forest, CA (US)

(73) Assignee: Exactech, Inc., Gainesville, FL (US)

( * ) Notice: Subject to any disclaimer, the term of this patent is extended or adjusted under 35 U.S.C. 154(b) by 870 days.

(21) Appl. No.: 12/077,462

(22) Filed: Mar. 19, 2008

(65) Prior Publication Data

US 2008/0234678 A1 Sep. 25, 2008

Related U.S. Application Data

(60) Provisional application No. 60/919,198, filed on Mar. 20, 2007.

(51) Int. Cl.
*A61B 17/70* (2006.01)

(52) U.S. Cl. .................. 606/86 A; 606/246; 606/279

(58) Field of Classification Search ........................ None
See application file for complete search history.

(56) References Cited

U.S. PATENT DOCUMENTS

| | | | |
|---|---|---|---|
| 602,580 A | 4/1898 | Haskins et al. | |
| 802,844 A | 10/1905 | Covell et al. | |
| 2,790,437 A | 4/1957 | Moore | |
| 4,545,374 A | 10/1985 | Jacobson | |
| 4,611,582 A | 9/1986 | Duff | |
| 4,743,260 A | 5/1988 | Burton | |
| 4,858,601 A | 8/1989 | Glisson | |
| 4,959,064 A | 9/1990 | Engelhardt | |
| 5,015,247 A | 5/1991 | Michelson | |

(Continued)

FOREIGN PATENT DOCUMENTS

EP 0767636 4/1997

(Continued)

OTHER PUBLICATIONS

International Search Report and Written Opinion for application No. PCT/US2008/085748, Mail Date Jun. 22, 2009, 12 pages.

(Continued)

*Primary Examiner* — Eduardo C Robert
*Assistant Examiner* — Nicholas Plionis
(74) *Attorney, Agent, or Firm* — Meyertons, Hood, Kivlin, Kowert & Goetzel, P.C.; Eric B. Meyertons

(57) ABSTRACT

A rod reduction instrument for position a rod relative to a seat of a bone anchor in a spinal implant system is provided. The instrument includes three concentric cannulas with circumferentially aligned rod receiving portions formed therein. One cannula is movable with respect to another to lock and unlock the seat of a bone anchor to the rod reduction instrument. The rod to be reduced is positioned inside at least one of the rod receiving portion. One cannula is moved with respect to another to lock the seat of the bone anchor to the rod reduction instrument. Once locked to the bone anchor, the remaining cannula is moved to reduce the distance between the rod and the seat within at least one of the rod receiving portions. The distance between the rod and the seat is reduced until the rod is position inside the seat. A secondary instrument is inserted through a central bore of the rod reduction instrument to introduce a cap and lock the cap to the seat securing the rod to the bone anchor.

25 Claims, 30 Drawing Sheets

U.S. PATENT DOCUMENTS

| | | |
|---|---|---|
| 5,062,845 A | 11/1991 | Kuslich et al. |
| 5,092,866 A | 3/1992 | Breard et al. |
| 5,129,388 A | 7/1992 | Vianaud et al. |
| 5,171,279 A | 12/1992 | Mathews |
| 5,180,393 A | 1/1993 | Commarmond et al. |
| 5,207,678 A | 5/1993 | Harms et al. |
| 5,282,863 A | 2/1994 | Burton |
| 5,368,594 A | 11/1994 | Martin et al. |
| 5,370,646 A | 12/1994 | Reese et al. |
| 5,375,823 A | 12/1994 | Navas et al. |
| 5,387,212 A | 2/1995 | Yuan et al. |
| 5,415,661 A | 5/1995 | Holmes |
| 5,437,669 A | 8/1995 | Yuan et al. |
| 5,437,672 A | 8/1995 | Alleyne |
| 5,443,467 A | 8/1995 | Biedermann |
| 5,449,355 A | 9/1995 | Rhum et al. |
| 5,474,555 A | 12/1995 | Puno et al. |
| 5,480,401 A | 1/1996 | Navas et al. |
| 5,484,437 A | 1/1996 | Michelson |
| 5,489,308 A | 2/1996 | Kuslich et al. |
| 5,522,843 A | 6/1996 | Zang |
| 5,527,312 A | 6/1996 | Ray |
| 5,540,688 A | 7/1996 | Navas et al. |
| 5,571,191 A | 11/1996 | Fitz |
| 5,609,636 A | 3/1997 | Kohrs et al. |
| 5,616,142 A | 4/1997 | Yuan et al. |
| 5,645,599 A | 7/1997 | Samani et al. |
| 5,658,337 A | 8/1997 | Kohrs et al. |
| 5,672,175 A | 9/1997 | Martin |
| 5,720,751 A | 2/1998 | Jackson |
| 5,741,253 A | 4/1998 | Michelson |
| 5,776,135 A | 7/1998 | Errico et al. |
| 5,885,286 A | 3/1999 | Sherman et al. |
| 5,891,145 A | 4/1999 | Morrison et al. |
| RE36,211 E | 5/1999 | Nonomura |
| 5,964,761 A | 10/1999 | Kambin |
| 6,004,327 A | 12/1999 | Asnis et al. |
| 6,014,588 A | 1/2000 | Fitz |
| 6,033,406 A | 3/2000 | Mathews |
| 6,063,088 A | 5/2000 | Winslow |
| RE36,758 E | 6/2000 | Fitz |
| 6,080,155 A | 6/2000 | Michelson |
| 6,080,157 A | 6/2000 | Cathro et al. |
| 6,096,038 A | 8/2000 | Michelson |
| 6,132,464 A | 10/2000 | Martin et al. |
| 6,200,322 B1 | 3/2001 | Branch et al. |
| 6,241,730 B1 | 6/2001 | Alby et al. |
| 6,248,105 B1 | 6/2001 | Schlapfer et al. |
| 6,261,293 B1 | 7/2001 | Nicholson et al. |
| 6,264,656 B1 | 7/2001 | Michelson |
| 6,267,764 B1 | 7/2001 | Elbera et al. |
| 6,267,765 B1 | 7/2001 | Taylor et al. |
| 6,270,498 B1 | 8/2001 | Michelson |
| 6,287,764 B1 | 9/2001 | Hildebrand et al. |
| 6,290,724 B1 | 9/2001 | Marino |
| 6,304,140 B1 | 10/2001 | Thron et al. |
| 6,306,140 B1 | 10/2001 | Siddiqui |
| 6,348,053 B1 | 2/2002 | Cachia |
| 6,375,657 B1 | 4/2002 | Doubler et al. |
| 6,419,703 B1 | 7/2002 | Fallin et al. |
| 6,440,133 B1 | 8/2002 | Beale et al. |
| 6,478,798 B1 | 11/2002 | Howland |
| 6,485,491 B1 | 11/2002 | Farris et al. |
| 6,485,518 B1 | 11/2002 | Cornwall et al. |
| 6,530,929 B1 | 3/2003 | Justis et al. |
| 6,533,790 B1 | 3/2003 | Liu |
| 6,540,747 B1 | 4/2003 | Marino |
| 6,547,795 B2 | 4/2003 | Schneiderman |
| 6,554,830 B1 | 4/2003 | Chappius |
| 6,558,390 B2 | 5/2003 | Cragg |
| 6,562,046 B2 | 5/2003 | Sasso |
| 6,565,565 B1 | 5/2003 | Yuan et al. |
| 6,565,573 B1 | 5/2003 | Ferrante et al. |
| 6,565,605 B2 | 5/2003 | Goble et al. |
| 6,579,319 B2 | 6/2003 | Goble et al. |
| 6,610,091 B1 | 8/2003 | Reiley |
| 6,626,904 B1 | 9/2003 | Jammet et al. |
| 6,626,905 B1 | 9/2003 | Schmiel et al. |
| 6,626,944 B1 | 9/2003 | Taylor et al. |
| 6,645,207 B2 | 11/2003 | Dixon et al. |
| 6,645,248 B2 | 11/2003 | Casutt et al. |
| 6,648,888 B1 | 11/2003 | Shluzas |
| 6,660,006 B2 | 12/2003 | Markworth et al. |
| 6,669,697 B1 | 12/2003 | Pisharodi |
| 6,669,729 B2 | 12/2003 | Chin |
| 6,676,661 B1 | 1/2004 | Benlloch et al. |
| 6,695,842 B2 | 2/2004 | Zucherman et al. |
| 6,699,247 B2 | 3/2004 | Zucherman et al. |
| 6,702,817 B2 | 3/2004 | Beger et al. |
| 6,709,434 B1 | 3/2004 | Gournay et al. |
| 6,716,214 B1 | 4/2004 | Jackson |
| 6,716,245 B2 | 4/2004 | Pasquet et al. |
| 6,726,687 B2 | 4/2004 | Jackson |
| 6,726,689 B2 | 4/2004 | Jackson |
| 6,730,089 B2 | 5/2004 | Jackson |
| 6,740,086 B2 | 5/2004 | Richelsoph |
| 6,740,090 B1 | 5/2004 | Cragg et al. |
| 6,749,613 B1 | 6/2004 | Conchy et al. |
| 6,749,614 B2 | 6/2004 | Teitelbaum et al. |
| 6,761,720 B1 | 7/2004 | Seneqas et al. |
| 6,770,075 B2 | 8/2004 | Howland |
| 6,783,527 B2 | 8/2004 | Drewry et al. |
| 6,786,903 B2 | 9/2004 | Lin |
| 6,790,209 B2 | 9/2004 | Beale et al. |
| 6,793,656 B1 | 9/2004 | Mathews |
| 6,802,844 B2 | 10/2004 | Ferree |
| 6,802,845 B2 | 10/2004 | Shirado et al. |
| 6,805,697 B1 | 10/2004 | Helm et al. |
| 6,811,567 B2 | 11/2004 | Reilev |
| 6,821,277 B2 | 11/2004 | Teitelbaum |
| 6,835,205 B2 | 12/2004 | Atkinson et al. |
| 6,835,207 B2 | 12/2004 | Zacouto et al. |
| 6,869,433 B2 | 3/2005 | Glascott |
| 6,875,212 B2 | 4/2005 | Shaolian et al. |
| 6,884,244 B1 | 4/2005 | Jackson |
| 6,896,677 B1 | 5/2005 | Lin |
| 6,899,716 B2 | 5/2005 | Cragg |
| 6,902,580 B2 | 6/2005 | Fallin et al. |
| 6,949,123 B2 | 9/2005 | Reiley |
| 6,966,910 B2 | 11/2005 | Ritland |
| 6,966,930 B2 | 11/2005 | Arnin et al. |
| 6,974,478 B2 | 12/2005 | Reilev et al. |
| 6,989,011 B2 | 1/2006 | Paul et al. |
| 6,997,927 B2 | 2/2006 | Jackson |
| 7,008,422 B2 | 3/2006 | Foley et al. |
| 7,011,660 B2 | 3/2006 | Sherman et al. |
| 7,011,685 B2 | 3/2006 | Arnin et al. |
| 7,029,475 B2 | 4/2006 | Paniabi |
| 7,033,358 B2 | 4/2006 | Taylor et al. |
| 7,041,136 B2 | 5/2006 | Goble et al. |
| 7,051,451 B2 | 5/2006 | Auaostino et al. |
| 7,052,497 B2 | 5/2006 | Sherman et al. |
| 7,060,068 B2 | 6/2006 | Tromanhauser et al. |
| 7,066,939 B2 | 6/2006 | Taylor |
| 7,066,957 B2 | 6/2006 | Graf et al. |
| 7,070,598 B2 | 7/2006 | Lim et al. |
| 7,074,237 B2 | 7/2006 | Goble et al. |
| 7,074,238 B2 | 7/2006 | Stinson et al. |
| 7,079,883 B2 | 7/2006 | Marino et al. |
| 7,081,117 B2 | 7/2006 | Bono et al. |
| 7,083,621 B2 | 8/2006 | Shaolian et al. |
| 7,083,622 B2 | 8/2006 | Simonson |
| 7,083,649 B2 | 8/2006 | Zucherman et al. |
| 7,087,055 B2 | 8/2006 | Lim et al. |
| 7,087,057 B2 | 8/2006 | Konieczynski et al. |
| 7,087,084 B2 | 8/2006 | Reiley |
| 7,090,698 B2 | 8/2006 | Goble et al. |
| 7,101,398 B2 | 9/2006 | Dooris et al. |
| 7,108,705 B2 | 9/2006 | Davison et al. |
| 7,125,410 B2 | 10/2006 | Freudiger et al. |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,156,849 B2 | 1/2007 | Dunbar et al. |
| 7,160,300 B2 | 1/2007 | Jackson |
| 7,182,783 B2 | 2/2007 | Trieu |

| | | |
|---|---|---|
| 7,188,626 B2 | 3/2007 | Foley et al. |
| 7,204,853 B2 | 4/2007 | Gordon et al. |
| 7,207,992 B2 | 4/2007 | Ritland |
| 7,214,227 B2 | 5/2007 | Colleran et al. |
| 7,220,262 B1 | 5/2007 | Hynes |
| 7,229,441 B2 | 6/2007 | Trieu et al. |
| 7,250,052 B2 | 7/2007 | Landry et al. |
| 7,261,688 B2 | 8/2007 | Smith et al. |
| 7,278,995 B2 | 10/2007 | Nichols et al. |
| 7,282,065 B2 | 10/2007 | Kirschman |
| 7,291,150 B2 | 11/2007 | Graf et al. |
| 7,291,153 B2 | 11/2007 | Glascott |
| 7,294,129 B2 | 11/2007 | Hawkins et al. |
| 7,306,603 B2 | 12/2007 | Boehm, Jr. et al. |
| 7,329,258 B2 | 2/2008 | Studer et al. |
| 7,335,200 B2 | 2/2008 | Carli et al. |
| 7,354,453 B2 | 4/2008 | McAfee |
| 7,361,196 B2 | 4/2008 | Fallin et al. |
| 7,371,238 B2 | 5/2008 | Soboleski et al. |
| 7,377,921 B2 | 5/2008 | Studer et al. |
| 7,377,942 B2 | 5/2008 | Berry |
| 7,406,775 B2 | 8/2008 | Funk et al. |
| 7,445,635 B2 | 11/2008 | Fallin et al. |
| 7,465,306 B2 | 12/2008 | Pond, Jr. et al. |
| 7,470,279 B2 | 12/2008 | Jackson |
| 7,476,238 B2 | 1/2009 | Panjabi |
| 7,491,218 B2 | 2/2009 | Landry et al. |
| 7,493,019 B2 | 2/2009 | Moon et al. |
| 7,503,918 B2 | 3/2009 | Baccelli et al. |
| 7,527,638 B2 | 5/2009 | Anderson et al. |
| 7,547,318 B2 | 6/2009 | Birkmeyer et al. |
| 7,563,264 B2 | 7/2009 | Landry et al. |
| 7,588,575 B2 | 9/2009 | Colleran et al. |
| 7,588,588 B2 | 9/2009 | Spitler et al. |
| 7,591,839 B2 | 9/2009 | Biedermann et al. |
| 7,615,068 B2 | 11/2009 | Timm et al. |
| 7,618,442 B2 | 11/2009 | Spitler et al. |
| 7,635,379 B2 | 12/2009 | Callahan et al. |
| 7,662,172 B2 | 2/2010 | Warnick |
| 7,678,137 B2 | 3/2010 | Butler et al. |
| 7,699,875 B2 | 4/2010 | Timm |
| 7,713,287 B2 | 5/2010 | Timm et al. |
| 7,713,288 B2 | 5/2010 | Timm et al. |
| 7,935,134 B2 | 5/2011 | Reglos et al. |
| 8,025,680 B2 | 9/2011 | Hayes et al. |
| 2001/0037111 A1 | 11/2001 | Dixon et al. |
| 2002/0026193 A1 | 2/2002 | Barker et al. |
| 2002/0032443 A1 | 3/2002 | Sherman et al. |
| 2002/0065557 A1 | 5/2002 | Goble et al. |
| 2002/0068975 A1 | 6/2002 | Teitelbaum et al. |
| 2002/0072800 A1 | 6/2002 | Goble et al. |
| 2002/0082599 A1 | 6/2002 | Crandall et al. |
| 2002/0082600 A1 | 6/2002 | Shaolian et al. |
| 2002/0091390 A1 * | 7/2002 | Michelson ............... 606/61 |
| 2002/0095154 A1 | 7/2002 | Atkinson |
| 2002/0123806 A1 | 9/2002 | Reiley |
| 2002/0133154 A1 | 9/2002 | Saint Martin |
| 2002/0133155 A1 | 9/2002 | Ferree |
| 2002/0151895 A1 | 10/2002 | Soboleski et al. |
| 2002/0161368 A1 | 10/2002 | Foley et al. |
| 2002/0161370 A1 | 10/2002 | Frigg et al. |
| 2002/0173971 A1 | 11/2002 | Stirpe et al. |
| 2002/0183748 A1 | 12/2002 | Martin et al. |
| 2002/0198526 A1 | 12/2002 | Shaolian et al. |
| 2003/0004511 A1 | 1/2003 | Ferree |
| 2003/0004512 A1 | 1/2003 | Farris et al. |
| 2003/0004572 A1 | 1/2003 | Goble et al. |
| 2003/0018350 A1 | 1/2003 | Zucherman et al. |
| 2003/0023240 A1 | 1/2003 | Amrein et al. |
| 2003/0028250 A1 | 2/2003 | Reiley et al. |
| 2003/0032957 A1 | 2/2003 | McKinley |
| 2003/0032965 A1 | 2/2003 | Schneiderman |
| 2003/0040797 A1 | 2/2003 | Fallin et al. |
| 2003/0045878 A1 | 3/2003 | Petit et al. |
| 2003/0055426 A1 | 3/2003 | Carbone et al. |
| 2003/0055427 A1 | 3/2003 | Graf |
| 2003/0073996 A1 | 4/2003 | Doubler et al. |
| 2003/0073997 A1 | 4/2003 | Doubler et al. |
| 2003/0073998 A1 | 4/2003 | Pagliuca et al. |
| 2003/0125741 A1 | 7/2003 | Biedermann et al. |
| 2003/0149431 A1 | 8/2003 | Varieur |
| 2003/0153912 A1 | 8/2003 | Graf |
| 2003/0163133 A1 | 8/2003 | Altarac et al. |
| 2003/0171749 A1 | 9/2003 | Le Couedic et al. |
| 2003/0171750 A1 | 9/2003 | Chin |
| 2003/0199872 A1 * | 10/2003 | Markworth et al. ............ 606/61 |
| 2003/0208202 A1 | 11/2003 | Falahee |
| 2003/0208203 A1 | 11/2003 | Lim et al. |
| 2003/0216735 A1 | 11/2003 | Altarac et al. |
| 2003/0220643 A1 | 11/2003 | Ferree |
| 2003/0229347 A1 | 12/2003 | Sherman et al. |
| 2004/0002708 A1 | 1/2004 | Ritland |
| 2004/0006341 A1 | 1/2004 | Shaolian et al. |
| 2004/0006344 A1 | 1/2004 | Nguyen et al. |
| 2004/0006391 A1 | 1/2004 | Reiley |
| 2004/0039384 A1 | 2/2004 | Boehm |
| 2004/0049189 A1 | 3/2004 | Le Couedic et al. |
| 2004/0049281 A1 | 3/2004 | Reiley |
| 2004/0064140 A1 | 4/2004 | Taylor et al. |
| 2004/0080418 A1 | 4/2004 | Dahlborn et al. |
| 2004/0082954 A1 | 4/2004 | Teitelbaum et al. |
| 2004/0087947 A1 | 5/2004 | Lim et al. |
| 2004/0092931 A1 | 5/2004 | Taylor et al. |
| 2004/0097933 A1 | 5/2004 | Lourdel et al. |
| 2004/0116927 A1 | 6/2004 | Graf |
| 2004/0127989 A1 | 7/2004 | Dooris et al. |
| 2004/0133208 A1 | 7/2004 | Weikel et al. |
| 2004/0138662 A1 | 7/2004 | Landry et al. |
| 2004/0143265 A1 | 7/2004 | Landry et al. |
| 2004/0143270 A1 | 7/2004 | Zucherman et al. |
| 2004/0147928 A1 | 7/2004 | Landry et al. |
| 2004/0147936 A1 | 7/2004 | Rosenberg et al. |
| 2004/0147937 A1 | 7/2004 | Dunbar et al. |
| 2004/0215190 A1 | 10/2004 | Nguyen et al. |
| 2004/0225289 A1 | 11/2004 | Biedermann et al. |
| 2004/0230201 A1 | 11/2004 | Yuan et al. |
| 2004/0230304 A1 | 11/2004 | Yuan et al. |
| 2004/0236328 A1 | 11/2004 | Paul et al. |
| 2004/0236329 A1 | 11/2004 | Panjabi |
| 2004/0243126 A1 | 12/2004 | Carbone et al. |
| 2004/0249378 A1 | 12/2004 | Saint Martin et al. |
| 2004/0249380 A1 | 12/2004 | Glascott |
| 2004/0267260 A1 | 12/2004 | Mack et al. |
| 2005/0010217 A1 | 1/2005 | Dalton |
| 2005/0010953 A1 | 1/2005 | Carney et al. |
| 2005/0010954 A1 | 1/2005 | Binder |
| 2005/0010956 A1 | 1/2005 | Moon et al. |
| 2005/0021031 A1 | 1/2005 | Folev et al. |
| 2005/0027361 A1 | 2/2005 | Reilev |
| 2005/0033295 A1 | 2/2005 | Wisnewski |
| 2005/0033434 A1 | 2/2005 | Berry |
| 2005/0033436 A1 | 2/2005 | Schlapfer et al. |
| 2005/0033439 A1 | 2/2005 | Gordon et al. |
| 2005/0038429 A1 | 2/2005 | Elsebaie |
| 2005/0038430 A1 | 2/2005 | McKinley |
| 2005/0038432 A1 | 2/2005 | Shaolian et al. |
| 2005/0038440 A1 | 2/2005 | Larson et al. |
| 2005/0043742 A1 | 2/2005 | Bruneau et al. |
| 2005/0043797 A1 | 2/2005 | Lee |
| 2005/0043799 A1 | 2/2005 | Reilev |
| 2005/0049588 A1 | 3/2005 | Jackson |
| 2005/0049589 A1 | 3/2005 | Jackson |
| 2005/0049705 A1 | 3/2005 | Hale et al. |
| 2005/0049708 A1 | 3/2005 | Atkinson et al. |
| 2005/0055031 A1 | 3/2005 | Lim |
| 2005/0055096 A1 | 3/2005 | Serhan et al. |
| 2005/0065515 A1 | 3/2005 | Jahng |
| 2005/0065516 A1 | 3/2005 | Jahng |
| 2005/0065517 A1 | 3/2005 | Chin |
| 2005/0070917 A1 | 3/2005 | Justis |
| 2005/0080418 A1 | 4/2005 | Simonson et al. |
| 2005/0080486 A1 | 4/2005 | Fallin et al. |
| 2005/0085813 A1 | 4/2005 | Spitler et al. |
| 2005/0085815 A1 | 4/2005 | Harms et al. |
| 2005/0101953 A1 | 5/2005 | Simonson |
| 2005/0101954 A1 | 5/2005 | Simonson |
| 2005/0101956 A1 | 5/2005 | Simonson |
| 2005/0113832 A1 | 5/2005 | Molz, IV et al. |

| Pub. No. | Date | Inventor |
|---|---|---|
| 2005/0113927 A1 | 5/2005 | Malek |
| 2005/0119748 A1 | 6/2005 | Reiley et al. |
| 2005/0124991 A1 | 6/2005 | Jahng |
| 2005/0125066 A1 | 6/2005 | McAfee |
| 2005/0131405 A1 | 6/2005 | Molz et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131409 A1 | 6/2005 | Chervitz et al. |
| 2005/0131422 A1 | 6/2005 | Anderson et al. |
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0137602 A1 | 6/2005 | Assell et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154461 A1 | 7/2005 | Humphreys et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0165396 A1 | 7/2005 | Fortin et al. |
| 2005/0171543 A1 | 8/2005 | Timm et al. |
| 2005/0171608 A1 | 8/2005 | Peterman et al. |
| 2005/0171609 A1 | 8/2005 | Humphrevs et al. |
| 2005/0171610 A1 | 8/2005 | Humphreys et al. |
| 2005/0177156 A1 | 8/2005 | Timm et al. |
| 2005/0177157 A1 | 8/2005 | Jahnq |
| 2005/0177164 A1 | 8/2005 | Walters et al. |
| 2005/0177166 A1 | 8/2005 | Timm et al. |
| 2005/0177240 A1 | 8/2005 | Blain |
| 2005/0182400 A1 | 8/2005 | White |
| 2005/0182401 A1 | 8/2005 | Timm et al. |
| 2005/0182409 A1 | 8/2005 | Callahan et al. |
| 2005/0187548 A1 | 8/2005 | Butler |
| 2005/0192570 A1* | 9/2005 | Jackson .................. 606/61 |
| 2005/0192574 A1 | 9/2005 | Blain |
| 2005/0192587 A1 | 9/2005 | Lim |
| 2005/0197700 A1 | 9/2005 | Boehm et al. |
| 2005/0197705 A1 | 9/2005 | Arnin et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0209593 A1 | 9/2005 | Kolb |
| 2005/0209694 A1 | 9/2005 | Loeb |
| 2005/0215999 A1 | 9/2005 | Birkmeyer et al. |
| 2005/0216000 A1 | 9/2005 | Colleran et al. |
| 2005/0222569 A1 | 10/2005 | Paniabi |
| 2005/0228378 A1 | 10/2005 | Kalfas et al. |
| 2005/0228381 A1 | 10/2005 | Kirschman |
| 2005/0234551 A1 | 10/2005 | Fallin et al. |
| 2005/0235508 A1 | 10/2005 | Augostino et al. |
| 2005/0240264 A1 | 10/2005 | Tokish et al. |
| 2005/0240265 A1 | 10/2005 | Kuioer et al. |
| 2005/0245928 A1 | 11/2005 | Colleran et al. |
| 2005/0245930 A1 | 11/2005 | Timm et al. |
| 2005/0249697 A1 | 11/2005 | Ulrich et al. |
| 2005/0261682 A1 | 11/2005 | Ferree |
| 2005/0261768 A1 | 11/2005 | Trieu |
| 2005/0273167 A1 | 12/2005 | Triolett et al. |
| 2005/0277921 A1 | 12/2005 | Eisermann et al. |
| 2005/0277922 A1 | 12/2005 | Trieu et al. |
| 2005/0288670 A1 | 12/2005 | Paniabi et al. |
| 2006/0004449 A1 | 1/2006 | Goble et al. |
| 2006/0004451 A1 | 1/2006 | Goble et al. |
| 2006/0015100 A1 | 1/2006 | Paniabi et al. |
| 2006/0025769 A1* | 2/2006 | Dick et al. .................. 606/61 |
| 2006/0036240 A1 | 2/2006 | Colleran et al. |
| 2006/0036244 A1 | 2/2006 | Soitler et al. |
| 2006/0036255 A1 | 2/2006 | Pond, Jr. et al. |
| 2006/0036260 A1 | 2/2006 | Runco et al. |
| 2006/0052785 A1 | 3/2006 | Auaostino et al. |
| 2006/0058791 A1 | 3/2006 | Broman et al. |
| 2006/0069391 A1 | 3/2006 | Jackson |
| 2006/0079894 A1 | 4/2006 | Colleran et al. |
| 2006/0079909 A1 | 4/2006 | Runco et al. |
| 2006/0084976 A1 | 4/2006 | Borgstrom et al. |
| 2006/0084982 A1 | 4/2006 | Kim |
| 2006/0084984 A1 | 4/2006 | Kim |
| 2006/0084987 A1 | 4/2006 | Kim |
| 2006/0084991 A1 | 4/2006 | Borastrom et al. |
| 2006/0085072 A1 | 4/2006 | Funk et al. |
| 2006/0106380 A1 | 5/2006 | Colleran |
| 2006/0106394 A1 | 5/2006 | Colleran |
| 2006/0111713 A1 | 5/2006 | Jackson |
| 2006/0142759 A1 | 6/2006 | Arnin et al. |
| 2006/0142761 A1 | 6/2006 | Landry et al. |
| 2006/0149238 A1 | 7/2006 | Sherman et al. |
| 2006/0149239 A1 | 7/2006 | Winslow et al. |
| 2006/0149254 A1 | 7/2006 | Laurvssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0149375 A1 | 7/2006 | Yuan et al. |
| 2006/0195086 A1 | 8/2006 | Sybert |
| 2006/0200137 A1 | 9/2006 | Soboleski et al. |
| 2006/0217718 A1 | 9/2006 | Chervitz et al. |
| 2006/0217719 A1 | 9/2006 | Albert et al. |
| 2006/0229616 A1 | 10/2006 | Albert et al. |
| 2006/0235388 A1 | 10/2006 | Justis et al. |
| 2006/0235393 A1 | 10/2006 | Bono et al. |
| 2006/0235414 A1 | 10/2006 | Lim et al. |
| 2006/0241593 A1 | 10/2006 | Sherman et al. |
| 2006/0241595 A1 | 10/2006 | Molz, IV et al. |
| 2006/0241597 A1 | 10/2006 | Mitchell et al. |
| 2006/0241599 A1 | 10/2006 | Konieczynski et al. |
| 2006/0241642 A1 | 10/2006 | Amin et al. |
| 2006/0241758 A1 | 10/2006 | Peterman et al. |
| 2006/0241759 A1 | 10/2006 | Trieu |
| 2006/0241768 A1 | 10/2006 | Trieu |
| 2006/0241769 A1 | 10/2006 | Gordon et al. |
| 2006/0247623 A1 | 11/2006 | Anderson et al. |
| 2006/0247628 A1 | 11/2006 | Rawlins et al. |
| 2006/0247630 A1 | 11/2006 | Iott et al. |
| 2006/0247632 A1 | 11/2006 | Winslow et al. |
| 2006/0247633 A1 | 11/2006 | Winslow et al. |
| 2006/0247637 A1 | 11/2006 | Colleran et al. |
| 2006/0247649 A1* | 11/2006 | Rezach et al. .................. 606/90 |
| 2006/0247650 A1 | 11/2006 | Yerby et al. |
| 2006/0247658 A1 | 11/2006 | Pond, Jr. et al. |
| 2006/0247769 A1 | 11/2006 | Molz et al. |
| 2006/0247773 A1 | 11/2006 | Stamp |
| 2006/0260483 A1 | 11/2006 | Hartmann et al. |
| 2006/0264934 A1 | 11/2006 | Fallin |
| 2006/0264962 A1 | 11/2006 | Chin et al. |
| 2006/0265069 A1 | 11/2006 | Goble et al. |
| 2006/0271198 A1 | 11/2006 | McAfee |
| 2006/0276798 A1 | 12/2006 | Lim |
| 2006/0276801 A1 | 12/2006 | Yerby et al. |
| 2006/0276897 A1 | 12/2006 | Winslow et al. |
| 2006/0282075 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert et al. |
| 2006/0293657 A1 | 12/2006 | Hartmann |
| 2006/0293690 A1 | 12/2006 | Abdelgany |
| 2006/0293692 A1 | 12/2006 | Whipple et al. |
| 2007/0005062 A1 | 1/2007 | Lanoe et al. |
| 2007/0005063 A1 | 1/2007 | Bruneau et al. |
| 2007/0016191 A1 | 1/2007 | Culbert et al. |
| 2007/0016193 A1 | 1/2007 | Ritland |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0016296 A1 | 1/2007 | Triplett et al. |
| 2007/0043358 A1 | 2/2007 | Molz, IV et al. |
| 2007/0043359 A1 | 2/2007 | Altarac et al. |
| 2007/0049931 A1 | 3/2007 | Justis et al. |
| 2007/0055242 A1 | 3/2007 | Bailly |
| 2007/0055257 A1 | 3/2007 | Vaccaro et al. |

| Publication No. | Date | Inventor |
|---|---|---|
| 2007/0073289 A1 | 3/2007 | Kwak et al. |
| 2007/0073396 A1 | 3/2007 | Arnin |
| 2007/0083264 A1 | 4/2007 | Arnin et al. |
| 2007/0090238 A1 | 4/2007 | Justis |
| 2007/0093816 A1 | 4/2007 | Arnin et al. |
| 2007/0100341 A1 | 5/2007 | Reqlos et al. |
| 2007/0118120 A1 | 5/2007 | A. Farris et al. |
| 2007/0118132 A1 | 5/2007 | Culbert et al. |
| 2007/0123861 A1 | 5/2007 | Dewey et al. |
| 2007/0123863 A1 | 5/2007 | Winslow et al. |
| 2007/0123989 A1 | 5/2007 | Gfeller et al. |
| 2007/0135814 A1 | 6/2007 | Farris |
| 2007/0167949 A1 | 7/2007 | Altarac et al. |
| 2007/0173828 A1 | 7/2007 | Firkins et al. |
| 2007/0213722 A1 | 9/2007 | Jones et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0239159 A1 | 10/2007 | Altarac et al. |
| 2007/0255284 A1 | 11/2007 | Miller et al. |
| 2007/0270811 A1 | 11/2007 | Dewey |
| 2007/0270867 A1 | 11/2007 | Miller et al. |
| 2007/0270868 A1 | 11/2007 | Dewey |
| 2007/0270869 A1 | 11/2007 | Young et al. |
| 2007/0276379 A1 | 11/2007 | Miller et al. |
| 2008/0009864 A1 | 1/2008 | Forton et al. |
| 2008/0015601 A1 | 1/2008 | Castro et al. |
| 2008/0039839 A1 | 2/2008 | Songer et al. |
| 2008/0045957 A1 | 2/2008 | Landry et al. |
| 2008/0051787 A1 | 2/2008 | Reminton et al. |
| 2008/0065072 A1 | 3/2008 | Spitler et al. |
| 2008/0077136 A1 | 3/2008 | Triplett et al. |
| 2008/0077139 A1 | 3/2008 | Landry et al. |
| 2008/0077155 A1 | 3/2008 | Diederich et al. |
| 2008/0097441 A1 | 4/2008 | Hayes et al. |
| 2008/0177275 A1* | 7/2008 | Wing et al. ............... 606/99 |
| 2008/0183215 A1 | 7/2008 | Altarac et al. |
| 2008/0221626 A1 | 9/2008 | Butters et al. |
| 2008/0228233 A1 | 9/2008 | Hoffman et al. |
| 2008/0234765 A1 | 9/2008 | Frasier et al. |
| 2008/0243126 A1 | 10/2008 | Gutierrez et al. |
| 2008/0249372 A1 | 10/2008 | Reglos et al. |
| 2008/0249628 A1 | 10/2008 | Altarac et al. |
| 2008/0262554 A1 | 10/2008 | Hayes et al. |
| 2008/0306488 A1 | 12/2008 | Altarac et al. |
| 2008/0306489 A1 | 12/2008 | Altarac et al. |
| 2008/0306557 A1 | 12/2008 | Altarac et al. |
| 2008/0312692 A1 | 12/2008 | Brennan et al. |
| 2009/0030465 A1 | 1/2009 | Altarac et al. |
| 2009/0036929 A1 | 2/2009 | Reglos et al. |
| 2009/0082775 A1 | 3/2009 | Altarac et al. |
| 2009/0125032 A1 | 5/2009 | Gutierrez et al. |
| 2009/0125047 A1 | 5/2009 | Reglos et al. |
| 2009/0138056 A1 | 5/2009 | Anderson et al. |
| 2009/0177196 A1 | 7/2009 | Zlock et al. |
| 2009/0204155 A1 | 8/2009 | Aschmann |
| 2009/0216237 A1 | 8/2009 | Frezal et al. |
| 2009/0228045 A1 | 9/2009 | Hayes et al. |
| 2009/0228053 A1 | 9/2009 | Kolb et al. |
| 2009/0228054 A1 | 9/2009 | Hoffman et al. |
| 2009/0228055 A1 | 9/2009 | Jackson |
| 2010/0036423 A1 | 2/2010 | Hayes et al. |
| 2010/0174317 A1 | 7/2010 | Timm et al. |
| 2010/0222819 A1 | 9/2010 | Timm et al. |
| 2011/0144701 A1 | 6/2011 | Altarac et al. |
| 2011/0166610 A1 | 7/2011 | Altarac et al. |

FOREIGN PATENT DOCUMENTS

| | | |
|---|---|---|
| EP | 0951246 | 10/1999 |
| EP | 0986339 | 3/2000 |
| EP | 1056408 | 12/2000 |
| EP | 1138268 | 10/2001 |
| EP | 1145602 | 10/2001 |
| EP | 1303225 | 4/2003 |
| EP | 1399078 | 3/2004 |
| EP | 1415602 | 7/2005 |
| EP | 1415603 | 7/2005 |
| EP | 1128773 | 6/2006 |
| EP | 1459690 | 6/2006 |
| EP | 986338 | 7/2006 |
| EP | 1810624 | 7/2007 |
| FR | 2728454 | 6/1996 |
| WO | 9116018 | 10/1991 |
| WO | 9426192 | 11/1994 |
| WO | 9531158 | 11/1995 |
| WO | 9600049 | 1/1996 |
| WO | 9822033 | 5/1998 |
| WO | 9848717 | 11/1998 |
| WO | 9855038 | 12/1998 |
| WO | 0062684 | 10/2000 |
| WO | 2011017712 | 2/2001 |
| WO | 0130248 | 5/2001 |
| WO | 0141681 | 6/2001 |
| WO | 0238060 | 5/2002 |
| WO | 02065954 | 8/2002 |
| WO | 02067793 | 9/2002 |
| WO | 02102259 | 12/2002 |
| WO | 03047442 | 6/2003 |
| WO | 03075805 | 9/2003 |
| WO | 03094699 | 11/2003 |
| WO | 03101350 | 12/2003 |
| WO | 2004008949 | 1/2004 |
| WO | 2004047617 | 6/2004 |
| WO | 2004078221 A2 | 9/2004 |
| WO | 2004103227 | 12/2004 |
| WO | 2004103228 | 12/2004 |
| WO | 2005009301 | 2/2005 |
| WO | 2005013864 | 2/2005 |
| WO | 2005018471 | 3/2005 |
| WO | 2005030029 | 4/2005 |
| WO | 2005030031 | 4/2005 |
| WO | 2005030066 | 4/2005 |
| WO | 2005030067 | 4/2005 |
| WO | 2005030087 | 4/2005 |
| WO | 2005041799 | 5/2005 |
| WO | 2005044152 | 5/2005 |
| WO | 2005046515 | 5/2005 |
| WO | 2005053572 | 6/2005 |
| WO | 2005055874 | 6/2005 |
| WO | 2005060879 | 7/2005 |
| WO | 2005067824 | 7/2005 |
| WO | 2005070278 | 8/2005 |
| WO | 2005070349 | 8/2005 |
| WO | 2005070350 | 8/2005 |
| WO | 2005070351 | 8/2005 |
| WO | 2005070352 | 8/2005 |
| WO | 2005070353 | 8/2005 |
| WO | 2005070354 | 8/2005 |
| WO | 2005076974 | 8/2005 |
| WO | 2005077113 | 8/2005 |
| WO | 2005079426 | 9/2005 |
| WO | 2005079672 | 9/2005 |
| WO | 2005079711 | 9/2005 |
| WO | 2005084590 | 9/2005 |
| WO | 2005087121 | 9/2005 |
| WO | 2005092223 | 10/2005 |
| WO | 2005094704 | 10/2005 |
| WO | 2005096974 | 10/2005 |
| WO | 2005104998 | 11/2005 |
| WO | 2005117765 | 12/2005 |
| WO | 2005120401 | 12/2005 |
| WO | 2006016371 | 2/2006 |
| WO | 2006017507 | 2/2006 |
| WO | 2006023683 | 3/2006 |
| WO | 2006033659 | 3/2006 |
| WO | 2006039260 | 4/2006 |
| WO | 2006042188 | 4/2006 |
| WO | 2006042189 | 4/2006 |
| WO | 2006023671 | 5/2006 |
| WO | 2006047363 | 5/2006 |
| WO | 2006063083 | 6/2006 |
| WO | 2006063107 | 6/2006 |
| WO | 2006065774 | 6/2006 |
| WO | 2006067790 | 6/2006 |
| WO | 2006045091 | 8/2006 |
| WO | 2006055186 | 8/2006 |
| WO | 2006089237 | 8/2006 |
| WO | 2006096351 | 9/2006 |

| | | |
|---|---|---|
| WO | 2006096381 | 9/2006 |
| WO | 2006101655 | 9/2006 |
| WO | 2006102268 | 9/2006 |
| WO | 2006102443 | 9/2006 |
| WO | 2006104999 | 10/2006 |
| WO | 2006108067 | 10/2006 |
| WO | 2006109310 | 10/2006 |
| WO | 2006110796 | 10/2006 |
| WO | 2006113256 | 10/2006 |
| WO | 2006115954 | 11/2006 |
| WO | 2006116214 | 11/2006 |
| WO | 2006119151 | 11/2006 |
| WO | 2006119236 | 11/2006 |
| WO | 2006119237 | 11/2006 |
| WO | 2006119241 | 11/2006 |
| WO | 2006125142 | 11/2006 |
| WO | 2006135511 | 12/2006 |
| WO | 2007014119 | 2/2007 |
| WO | 2007021588 | 2/2007 |
| WO | 2007031998 | 3/2007 |
| WO | 2007034472 | 3/2007 |
| WO | 2007037801 | 4/2007 |
| WO | 2007038261 | 4/2007 |
| WO | 2007043044 | 4/2007 |
| WO | 2007075375 | 7/2007 |
| WO | 2007102846 A1 | 9/2007 |
| WO | 2007117366 | 10/2007 |
| WO | 2007121061 A2 | 10/2007 |
| WO | 2007127608 A1 | 11/2007 |
| WO | 2007127682 A1 | 11/2007 |
| WO | 2007136612 | 11/2007 |
| WO | 2008069835 | 6/2008 |
| WO | 2008115549 | 9/2008 |
| WO | 2008121421 | 10/2008 |
| WO | 2008124186 | 10/2008 |
| WO | 2008140756 | 11/2008 |
| WO | 2008153747 | 12/2008 |
| WO | 2009042489 | 4/2009 |
| WO | 2009049206 | 4/2009 |
| WO | 2009076239 | 6/2009 |
| WO | 2009091960 | 7/2009 |
| WO | 2009100190 | 8/2009 |
| WO | 2008121343 | 10/2009 |
| WO | 2010019791 | 2/2010 |
| WO | 2011028575 | 3/2011 |

OTHER PUBLICATIONS

Co-Pending U.S. Appl. No. 11/427,738 by Reglos et al entitled "Systems and Methods for Stabilization of Bone Structures" filed Jun. 29, 2006.
Co-Pending U.S. Appl. No. 11/436,407 by Hayes et al entitled "Systems and Methods for Posterior Dynamic Stabilization of the Spine" filed May 17, 2006.
First Examiner's Report for AU App. No. 2006272755 mailed May 31, 2011. (pp. 1-3).
Second Exmainer's Report for AU App. No. 2005295209 mailed Jun. 1, 2011. (pp. 1-3).
International Preliminary Report on Patentability and Written Opinion for PCT/US2008/004098, mailed Jul. 25, 2008. (pp. 1-7).
International Preliminary Report on Patentability and Written Opinion for PCT/US2008/03677, mailed Jul. 22, 2008. (pp. 1-9).
International Preliminary Report on Patentability and Written Opinion for PCT/US2008/079580, mailed Apr. 29, 2009. (pp. 1-6).
International Preliminary Report on Patentability and Written Opinion for PCT/US2009/053740, Feb. 21, 2011. (6 pages).
International Search Report and Written Opinion for PCT/US2006/28586, mailed Jul. 27, 2007. (pp. 1-14).
International Search Report and Written Opinion for PCT/US2005/038021, mailed Apr. 10, 2006 (pp. 1-6).
International Search Report and Written Opinion for PCT/US2007/004726, mailed Jul. 8, 2008. (pp. 1-6).
International Search Report and Written Opinion for PCT/US2007/11573, mailed Apr. 23, 2008. (pp. 1-6).
USPTO Communicaiton for U.S. Appl. No. 11/362,366 mailed Mar. 18, 2011.
International Search Report and Written Opinion for PCT/US2009/031225, mailed Aug. 31, 2009. (15 pages).
International Search Report for PCT/US2008/004098, mailed Jul. 25, 2008. (1 page).
International Search Report for PCT/US2008/03677, mailed Jul. 22, 2008. (1 page).
International Search Report for PCT/US2008/079580, mailed Apr. 29, 2009. (pp. 1-5).
International Search Report for PCT/US2009/053740, mailed Mar. 24, 2010. (pp. 1-4).
International Search Report for PCT/US2010/44930, mailed Apr. 1, 2011. (pp. 1-4).
Written Opinion for PCT/US2010/44930, mailed Mar. 31, 2009. (pp. 1-4).
USPTO Communicaiton for U.S. Appl. No. 10/970,366 mailed Nov. 25, 2008.
USPTO Communicaiton for U.S. Appl. No. 10/970,366 mailed Nov. 5, 2009.
USPTO Communicaiton for U.S. Appl. No. 11/006,495 mailed Dec. 29, 2009.
USPTO Communicaiton for U.S. Appl. No. 11/006,495 mailed Jun. 6, 2008.
USPTO Communicaiton for U.S. Appl. No. 11/006,495 mailed Mar. 20, 2009.
USPTO Communicaiton for U.S. Appl. No. 11/033,452 mailed Dec. 11, 2008.
USPTO Communicaiton for U.S. Appl. No. 11/033,452 mailed Oct. 13, 2009.
USPTO Communicaiton for U.S. Appl. No. 11/427,738 mailed Dec. 29, 2009.
USPTO Communicaiton for U.S. Appl. No. 11/436,407 mailed Jun. 21, 2009.
USPTO Communication for U.S. Appl. No. 11/006,495 mailed Jun. 30, 2008.
Co-Pending U.S. Appl. No. 11/586,849 by Altarac et al entitled "Systems and methods for stabilization of bone structures" filed Oct. 25, 2006.
USPTO Communicaiton for U.S. Appl. No. 11/586,849, mailed Jul. 8, 2011.
Co-Pending U.S. Appl. No. 11/726,093 by Altarac et al entitled "Screw systems and methods for use in stabilization of bone structures" filed Mar. 20, 2007.
USPTO Communication for U.S. Appl. No. 11/726,093, mailed Nov. 5, 2010.
USPTO Communication for U.S. Appl. No. 11/726,093, mailed May 12, 2011.
Co-Pending U.S. Appl. No. 12/355,093 by Reglos et al entitled "Tissue splitter" filed Jan. 16, 2009.
USPTO Communication for U.S. Appl. No. 12/355,093, mailed Jun. 27, 2011.
Co-Pending U.S. Appl. No. 12/966,807 by Altarac et al entitled "Methods for Stabilization of Bone Structures" filed Dec. 13, 2010.
Co-Pending U.S. Appl. No. 12/966,790 by Altarac et al entitled "Method for Stabilizing Bone Strucutres" filed Dec. 13, 2010.
USPTO Communicaiton for U.S. Appl. No. 11/362,366 mailed Apr. 23, 2010.
USPTO Communicaiton for U.S. Appl. No. 11/362,366 mailed Apr. 7, 2009.
Co-Pending U.S. Appl. No. 12/329,423 by Altarac et al entitled "Spondylolisthesis reduction system and method" filed Dec. 5, 2008.
Co-Pending U.S. Appl. No. 12/270,505 by Gutierrez et al entitled "Rod removal instrument" filed Nov. 13, 2008.
Co-Pending U.S. Appl. No. 12/853,260 by Altarac et al entitled "Systems and Methods for Stabilization of Bone Structures, Including Thorocolumbar Stabilization Systems and Methods" filed Aug. 9, 2010.
Co-pending U.S. Appl. No. 11/362,366 by Altarac et al. entitled "Systems and methods for stabilization of bone structures" filed Feb. 23, 2006.
USPTO Advisory Action for U.S. Appl. No. 11/726,093, mailed Aug. 30, 2011.
USPTO Notice of Allowance for U.S. Appl. No. 12/077,462, mailed Sep. 28, 2011.

USPTO Final Office Action for U.S. Appl. No. 11/362,366 mailed Oct. 27, 2011.
USPTO Non-Final Office Action for U.S. Appl. No. 12/329,423, mailed Nov. 30, 2011.

* cited by examiner

ROD REDUCER

CROSS REFERENCE TO RELATED APPLICATIONS

This application claims priority to and is a continuation-in-part of U.S. Provisional Patent Application Ser. No. 60/919,198 entitled "Rod reducer" filed on Mar. 20, 2007, hereby incorporated by reference in its entirety.

FIELD

The present invention generally relates to surgical instruments and methods for using these instruments. More particularly, but not exclusively, instruments and methods for correcting the positioning of and stabilizing one or more bone structures of the spine are disclosed.

BACKGROUND

In the field of orthopedic spinal surgery, it is well known to correct the positioning of and stabilization of the spine or to facilitate fusion at various levels of the spine after an injury, malformation, or other defect by use of implanted rod systems affixed to vertebral bodies of the spine. In one such system, one or more rods are disposed longitudinally along a length of the spine spanning two or more vertebral bodies. The rod is sometimes bent, either prior to or during surgery, to correspond to the normal curvature of the spine in the particular region being instrumented, or to such other curvature as the surgeon may deem appropriate to correct the defect. For example, the rod can be bent to form a kyphotic curvature for the thoracic region of the spine, or to form a lordotic curvature for the lumbar region. The rod is engaged to a number of fixation elements fixed to or engaged with the vertebrae along the spinal column.

A variety of fixation elements that are configured to engage the vertebrae can be utilized. For instance, one such fixation element is a polyaxial bone screw with a head or collar which can be threaded into a pedicle or other portion of the vertebral body. Typically, for single level fusion, two bone screws are implanted into adjacent vertebral bodies on one side of the spine and two bone screws are implanted in the same vertebral bodies on the other side of the spine. A rod is provided and coupled to the two bone screws along one side and another rod is provided and coupled to the two bone screws along the other side of the spine. The secured rods provide corrective and stabilizing forces to the spine.

Generally, affixing a rod to a bone screw requires the rod to be properly seated in the collar of the anchor assembly. In some cases, such as in patients with spondylolisthesis where there is an anteroposterior translatory movement of two spinal vertebrae in relation to each other due to instability between the two involved vertebrae, a rod and an implanted screw must be moved with respect to each other so that the rod occupies the space within a channel or other opening in a collar attached to the screw so that the rod can be coupled to the screw. The rod is then coupled to the implanted bone screw using a set screw, plug or other appropriate fastener that is inserted into an opening or channel of the seat. The process of placing a rod within or adjacent to an implanted fixation element so that they can be coupled together is termed "reducing" the rod because the rod and implanted fixation element are drawn together or caused to converge.

Rod reduction is commonly performed by a surgeon using his or her hands and/or rigid tools as pliers, levers or other instrumentation adaptable to create the necessary pushing and/or pulling forces on the implanted screw and rod in an open or mini-open surgical procedure. Such procedures generally require the surgeon to place the rod directly over the implanted fixation element and intersect the longitudinal axis of the fixation element. Consequently, access to the rod and the implanted fixation element along that axis and directly above the opening in the fixation element into which the rod is to be placed, is necessary. However, such access can be difficult depending on such factors as the degree to which the patient anatomy needs to be corrected and the overall physiology of the patient, and can be very difficult in procedures in which surgical invasiveness is to be minimized as a result of the small ports or incisions of such procedures. Additionally, the physiology of the patient can require that the screw be placed at an angle such that the surgeon would have difficulty accessing and exerting force in the necessary orientation on the rod and/or fixation element, especially if used with certain screw systems having seats with a limited range of motion. Also, screw systems that have an unsecured rod-receiving portion relative to the bone screw can make reduction a task in minimally invasive surgical procedures.

Hence, there is a need for rod reducing instruments that can be used efficiently, safely and securely in rod reduction procedures and there is a need for rod reduction instruments that can be used in both minimally invasive and open surgical approaches.

SUMMARY

According to one aspect of the invention a rod reduction instrument for positioning a rod relative to a seat of a bone anchor in a spinal implant system is disclosed. The instrument includes a body having a handle at a proximal end of the instrument. The instrument further includes an inner cannula having a first proximal end, a first distal end configured to receive a seat and a first longitudinal axis defining a first bore from the first proximal end to the first distal end. The inner cannula is connected to the body at the first proximal end such that it is movable with respect to the body. The inner cannula has a first rod channel opening at the first distal end and extending towards the first proximal end. The inner cannula has a seat clamp at the first distal end configured to lock the inner cannula to the seat of a bone anchor. The seat clamp comprises at least one deflectable member. The instrument further includes a middle cannula. The middle cannula has a second proximal end, a second distal end and a second longitudinal axis defining a second bore from the second proximal end to the second distal end. The middle cannula is connected to the body at the second proximal end. The middle cannula is positioned at least partially over the inner cannula and movable with respect to the inner cannula. The middle cannula has a second rod channel opening at the second distal end and extending towards the second proximal end. The second rod channel is circumferentially aligned with the first rod channel. The instrument further includes an outer cannula having a third proximal end, a third distal end and a third longitudinal axis defining a third bore from the third proximal end to the third distal end. The outer cannula is positioned at least partially over the middle cannula and movable with respect to the middle cannula. The outer cannula has a third rod channel opening at the third distal end and extending towards the third proximal end. The third rod channel is circumferentially aligned with the first and second rod channels. The instrument is configured to receive the seat of a bone anchor at the first distal end and is configured to lock the seat at the first distal end with movement of the instrument in a direction towards the seat such that such movement slides the middle cannula distally with respect to the inner cannula and over the at least one deflectable member to thereby deflect the at least one deflectable member inwardly towards the first longitudinal axis and lock the at least one deflectable member to the seat. Movement of the middle cannula proximally with respect to the inner cannula uncovers the at least one deflectable member allowing the deflectable member to spring away from the seat and the first longitudinal axis to thereby unlock the seat from the instrument. With the rod to be reduced located in one of the first or second rod channels and the seat received in the distal end, movement of the outer cannula distally with respect to the middle cannula slides the outer cannula over the middle cannula to engage the third rod channel with the rod and reduce the distance between the rod and the seat.

According to another aspect of the invention, a method for positioning a rod relative to a seat of a bone anchor in a spinal implant system is disclosed. The method includes the step of implanting the bone anchor having a seat to a vertebra of a spinal column. The rod is positioned adjacent to the bone anchor and a rod reduction instrument is provided. The rod reduction instrument includes a body having a handle at a proximal end of the instrument. The instrument further includes an inner cannula having a first proximal end, a first distal end configured to receive the seat and a first longitudinal axis defining a first bore from the first proximal end to the first distal end. The inner cannula is connected to the body at the first proximal end such that it is movable with respect to the body. The inner cannula has a first rod channel opening at the first distal end and extending towards the first proximal end. The inner cannula has a seat clamp at the first distal end that is configured to lock the inner cannula to the seat of a bone anchor. The seat clamp has at least one deflectable member. The instrument further includes a middle cannula having a second proximal end, a second distal end and a second longitudinal axis defining a second bore from the second proximal end to the second distal end. The middle cannula is connected to the body at the second proximal end. The middle cannula is positioned at least partially over the inner cannula and movable with respect to the inner cannula. The middle cannula has a second rod channel opening at the second distal end and extending towards the second proximal end. The second rod channel is substantially circumferentially aligned with the first rod channel. The rod reduction instrument further includes an outer cannula having a third proximal end, a third distal end and a third longitudinal axis defining a third bore from the third proximal end to the third distal end. The outer cannula is positioned at least partially over the middle cannula and movable with respect to the middle cannula. The outer cannula has a third rod channel opening at the third distal end and extending towards the third proximal end. The third rod channel is substantially circumferentially aligned with the first and second rod channels. The rod reduction instrument is positioned such that the rod is located in the first, second or third rod channel. The rod reduction instrument is moved towards the bone anchor. The first distal end of the rod reduction instrument is contacted to the seat such that the seat is aligned with at least one of the first, second or third rod channel. After contacting the first distal end of the rod reduction instrument to the seat, the rod reduction instrument is advanced towards the seat to lock the rod reduction instrument to the seat. The outer cannula is advanced over the middle cannula towards the seat to reduce the distance between the rod and the seat.

According to another aspect of the present invention, a rod reduction instrument for positioning a rod relative to a seat of a bone anchor in a spinal implant system is disclosed. The rod reduction instrument includes a body having a handle at the proximal end of the instrument, a seat receiving portion at the distal end of the instrument and a rod receiving portion opening at the distal end and extending towards the proximal end. The instrument further includes a seat locking feature configured to lock the rod reduction instrument to a seat in a single push down action by the user.

According to another aspect of the present invention, a rod reduction instrument for positioning a rod relative to a seat of a bone anchor in a spinal implant system is disclosed. The instrument includes a body having a handle at the proximal end of the instrument and a seat receiving portion at the distal end of the instrument. The instrument further includes a rod receiving portion opening at the distal end and extending towards the proximal end and a seat locking feature configured to releasably lock the rod reduction instrument to a seat. The instrument further includes a cannula movable with respect to the seat to reduce the distance between the seat and the rod and a cannula locking feature configured to releasably lock the position of the cannula wherein the cannula locking feature is independent from the seat locking feature.

According to yet another aspect of the present invention, rod reduction instrument for positioning a rod relative to a seat of a bone anchor in a spinal implant system is disclosed. The instrument includes a body having a handle at the proximal end of the instrument and a seat receiving portion at the distal end of the instrument configured to connect to the seat. The instrument includes a rod receiving portion opening at the distal end and extending at least partially towards the proximal end configured to receive a rod therein. The instrument further includes a cannula movable with respect to the body to reduce the distance between the seat and the rod. The instrument further includes a driver configured to translate the cannula. The driver has a removable driver handle. The removable handle is insertable into the driver on the left side of the instrument or on the right side of the instrument.

According to another aspect of the present invention, a rod reduction instrument for positioning a rod relative to a seat of a bone anchor in a spinal implant system is disclosed. The instrument includes a body having a handle at the proximal end of the instrument and a seat receiving portion at the distal end of the instrument configured to connect to the seat. The instrument includes a rod receiving portion opening at the distal end and extending towards the proximal end configured to receive a rod therein. The instrument further includes a cannula movable with respect to the body to reduce the distance between the seat and the rod. The instrument further includes a driver configured to move the cannula to reduce the distance between the seat and the rod. The driver has an indicator providing indication of the degree of reduction to the user.

According to another aspect of the invention, a rod reduction instrument for positioning a rod relative to a seat of a bone anchor in a spinal implant system is provided. The rod reduction instrument includes a body having a handle at the proximal end of the instrument and a seat receiving portion at the distal end of the instrument configured to connect to the seat. The instrument includes a rod receiving portion opening at the distal end and extending towards the proximal end configured to receive a rod therein. The instrument further includes a cannula movable with respect to the body to reduce the distance between the seat and the rod. The cannula is configured to engage the rod at the outer edges of the seat.

According to another aspect of the invention, a rod reduction instrument for positioning a rod relative to a seat of a bone anchor in a spinal implant system is disclosed. The instrument includes a body having a handle at the proximal end of the instrument and a seat receiving portion at the distal end of the instrument configured to connect to the seat. The instrument includes an elongated rod receiving portion opening at the distal end and extending at least partially towards the proximal end configured to receive a rod therein. The instrument further includes a cannula movable with respect to the body to reduce the distance between the seat and the rod and a bore opening at the proximal end of the instrument and extending to the distal end of the instrument. The central bore is in communication with the seat when connected thereto. The instrument further includes a secondary instrument insertable through the central bore of the instrument without removal of the rod reduction instrument from the seat.

According to another aspect of the invention, a method for positioning a rod relative to a seat of a bone anchor in a spinal implant system is disclosed. The method includes the step of engaging the bone anchor having a seat to a vertebra of a spinal column. A rod is positioned adjacent to the bone anchor and a rod reduction instrument is provided. The rod reduction instrument includes a body having a handle at the proximal end of the instrument and a seat receiving portion at the distal end of the instrument configured to connect to the seat. The instrument further includes an elongated rod receiving portion opening at the distal end and extending towards the proximal end configured to receive a rod therein and a cannula movable with respect to the body to reduce the distance between the seat and the rod. The instrument includes a bore opening at the proximal end of the instrument and extending to the distal end of the instrument. The bore is in communication with the seat when connected thereto. The rod reduction instrument is positioned such that the rod is located in the rod receiving portion. The rod reduction instrument is moved towards the bone anchor. The distal end of the rod reduction instrument is connected to the seat. The cannula is moved towards the seat to reduce the distance between the rod and the seat. A cap inserter having a cap attached thereto is inserted into proximal opening of the bore. The cap inserter is turned attaching the cap to the seat and the cap inserter is removed leaving the cap attached to the seat.

According to another aspect of the invention, a rod reduction instrument for position a rod relative to a seat of a bone anchor in a spinal implant system is provided. The instrument includes three concentric cannulas with circumferentially aligned rod receiving portions formed therein. One cannula is movable with respect to another to lock and unlock the seat of a bone anchor to the rod reduction instrument. The rod to be reduced is positioned inside at least one of the rod receiving portions. One cannula is moved with respect to another to lock the seat of the bone anchor to the rod reduction instrument. Once locked to the bone anchor, the remaining cannula is moved with respect to the other two cannulas to reduce the distance between the rod and the seat within at least one of the rod receiving portions. The distance between the rod and the seat is reduced until the rod is positioned inside the seat. A secondary instrument is inserted through a central bore of the rod reduction instrument to introduce a cap and lock the cap to the seat, thereby, securing the rod to the bone anchor.

Other advantages will be apparent from the description that follows, including the drawings and claims.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
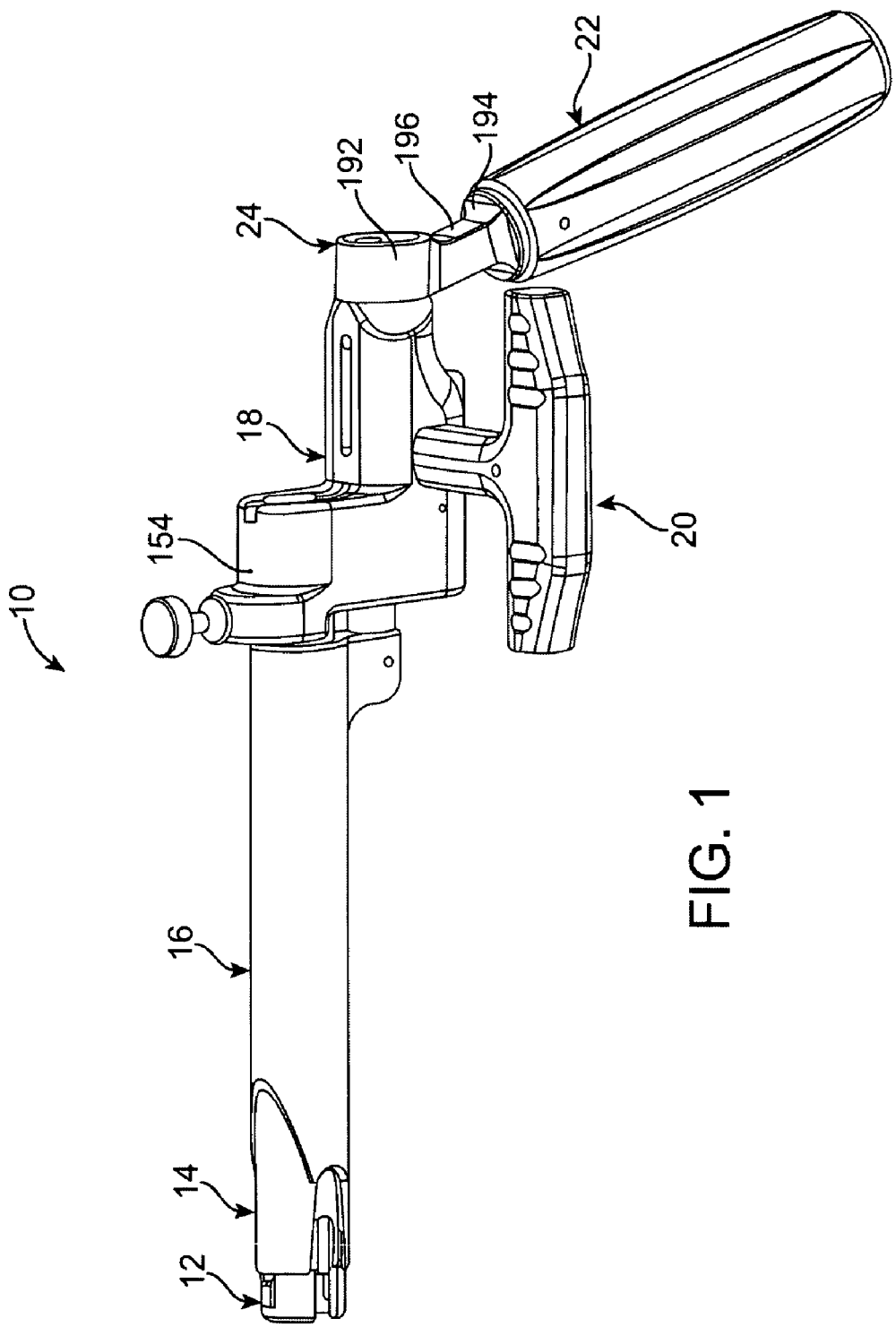
FIG. 1 is a perspective view of a rod reduction instrument according to an embodiment of the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention will now be described in detail by way of the following description of exemplary embodiments and variations of the systems and methods of the present invention. While more fully described in the context of the description of the subject methods of implanting the subject systems, it should be initially noted that in certain applications where the natural facet joints are compromised, inferior facets, lamina, posterior arch and spinous process of superior vertebra may be resected for purposes of implantation of certain of the dynamic stabilization systems of the present invention. In other applications, where possible, the natural facet joints, lamina and/or spinous processes are spared and left intact for implantation of other dynamic stabilization systems of the present invention.

It should also be understood that the term "system", when referring to a system of the present invention, most typically refers to a set of components which includes multiple bone stabilization components such as a superior, cephalad or rostral (towards the head) component configured for implantation into a superior vertebra of a vertebral motion segment and an inferior or caudal (towards the feet) component configured for implantation into an inferior vertebra of a vertebral motion segment. A pair of such component sets may include one set of components configured for implantation into and stabilization of the left side of a vertebral segment and another set configured for the implantation into and stabilization of the right side of a vertebral segment. Where multiple bone segments such as spinal segments or units are being treated, the term "system" may refer to two or more pairs of component sets, i.e., two or more left sets and/or two or more right sets of components. Such a multilevel system involves stacking of component sets in which each set includes a superior component, an inferior component, and one or more medial components therebetween.

The superior and inferior components (and any medial components therebetween), when operatively implanted, may be engaged or interface with each other in a manner that enables the treated spinal motion segment to mimic the function and movement of a healthy segment, or may simply fuse the segments such as to eliminate pain and/or promote or enhance healing. The interconnecting or interface means include one or more structures or members that enables, limits and/or otherwise selectively controls spinal or other body motion. The structures may perform such functions by exerting various forces on the system components, and thus on the target vertebrae. The manner of coupling, interfacing, engagement or interconnection between the subject system components may involve compression, distraction, rotation or torsion, or a combination thereof. In certain embodiments, the extent or degree of these forces or motions between the components may be intraoperatively selected and/or adjusted to address the condition being treated, to accommodate the particular spinal anatomy into which the system is implanted, and to achieve the desired therapeutic result.

In certain embodiments, the multiple components, such as superior and inferior spinal components, are mechanically coupled to each other by one or more interconnecting or interfacing means. In other embodiments, components interface in a manner that constrains their relative movement and enables the treated segment to mimic the function or partial function and/or movement or partial movement of a healthy segment. Typically, spinal interconnecting means is a dorsally positioned component, i.e., positioned posteriorly of the superior and inferior components, or may be a laterally positioned component, i.e., positioned to the outer side of the posterior and inferior components. The structures may include one or more struts and/or joints that provide for stabilized spinal motion. The various system embodiments may further include a band, interchangeably referred to as a ligament, which provides a tensioned relationship between the superior and inferior components and helps to maintain the proper relationship between the components.

Reference will now be made in detail to the present embodiments of the invention, examples of which are illustrated in the accompanying drawings. Wherever possible, the same reference numbers will be used throughout the drawings to refer to the same or like parts. In addition, each of the inventive embodiments described herein may be employed in a percutaneous procedure, a mini-open procedure or an open procedure. Utilization of minimally invasive techniques can shorten the procedure's time and speed recovery by the patient. However, the application of these inventions in a minimally invasive manner is not a requirement.

Figure 2:
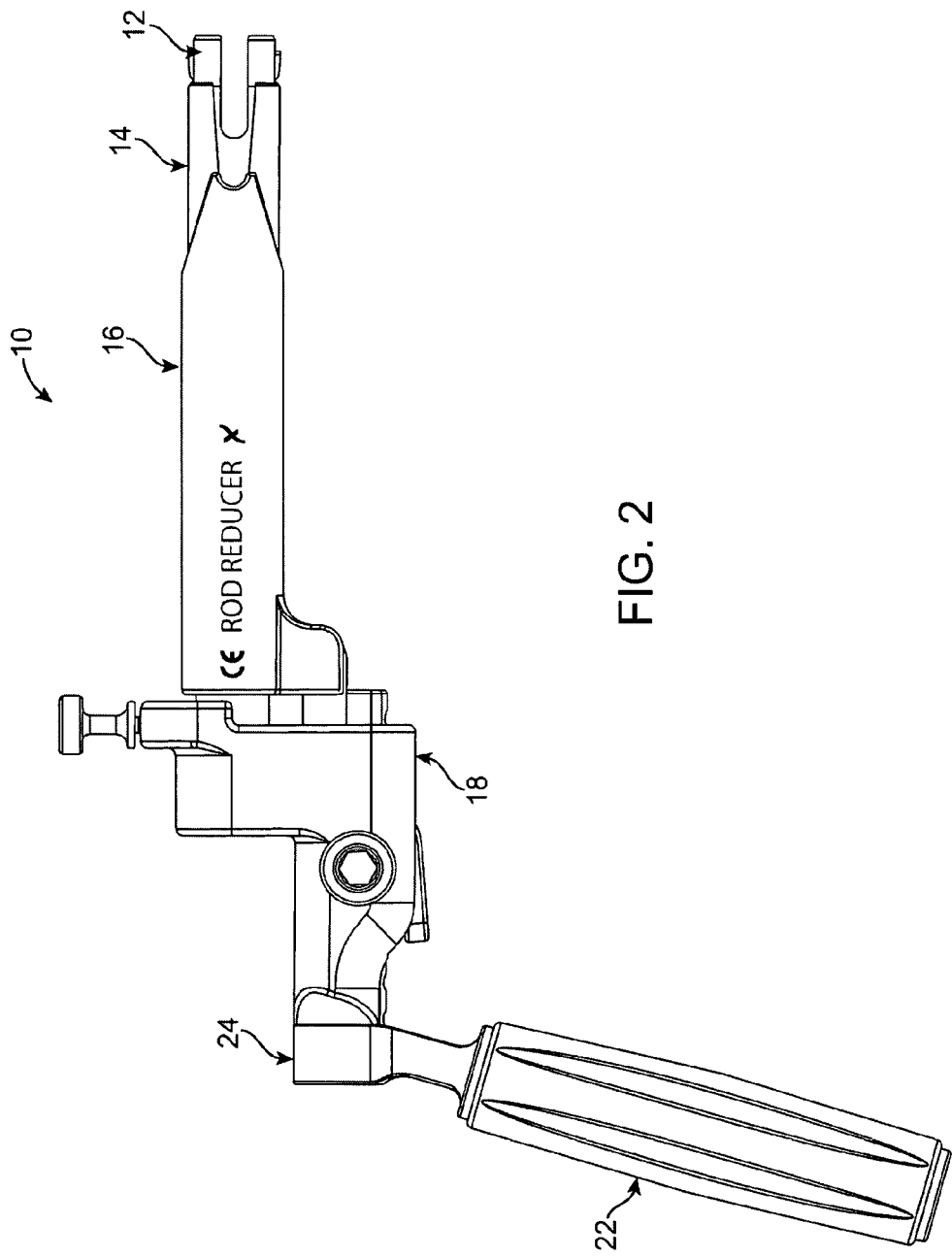
FIG. 2 is a side elevational view of a rod reduction instrument without the pinion driver attached to the instrument according to an embodiment of the present invention.

FIG. 1 shows a perspective view of a rod reduction instrument 10 according to the present invention. The rod reducer 10 includes an inner cannula assembly 12, a locking shaft (or middle cannula) 14, a plunger (or outer cannula) 16, a body assembly 18, a pinion driver 20, a handle 22, and a handle connector 24. The cannula assembly 12 is connected to the locking shaft 14 so that one of the cannula assembly 12 and locking shaft 14 is movable with respect to the other; the other one of the cannula assembly 12 and locking shaft 14 is connected to the body assembly 18. The cannula assembly 12 is configured such that it substantially fits inside the locking shaft 14. The plunger 16 is connected to the body assembly 18 such that it is movable with respect to cannula assembly 12 and the locking shaft 14. The handle 22 is connected to the handle connector 24 which is connected to the body assembly 18. The pinion driver 20 is removably inserted into the body assembly 18. FIG. 2 is a side elevational view of the rod reducer 10 without the pinion driver 20.

In normal use, the rod reducer instrument 10 is oriented so that the handle 22 is located proximally and accessible by the surgeon and the opposite end of the instrument 10 is oriented distally away from the surgeon and towards the operative site. The operative site is generally the spinal column of a patient and in particular, a vertebral body in which a bone screw system is located. A typical bone screw system is described in U.S. patent application Ser. No. 11/362,366 entitled "Systems and methods for stabilization of bone structures" filed on Feb. 23, 2006, U.S. patent application Ser. No. 11/586,849 entitled "Systems and methods for stabilization of bone structures" filed on Oct. 25, 2006 and U.S. patent application Ser. No. 11/726,093 entitled "Screw systems and methods for use in stabilization of bone structures" filed on Mar. 20, 2007 all incorporated herein by reference in their entirety.

Figure 3:
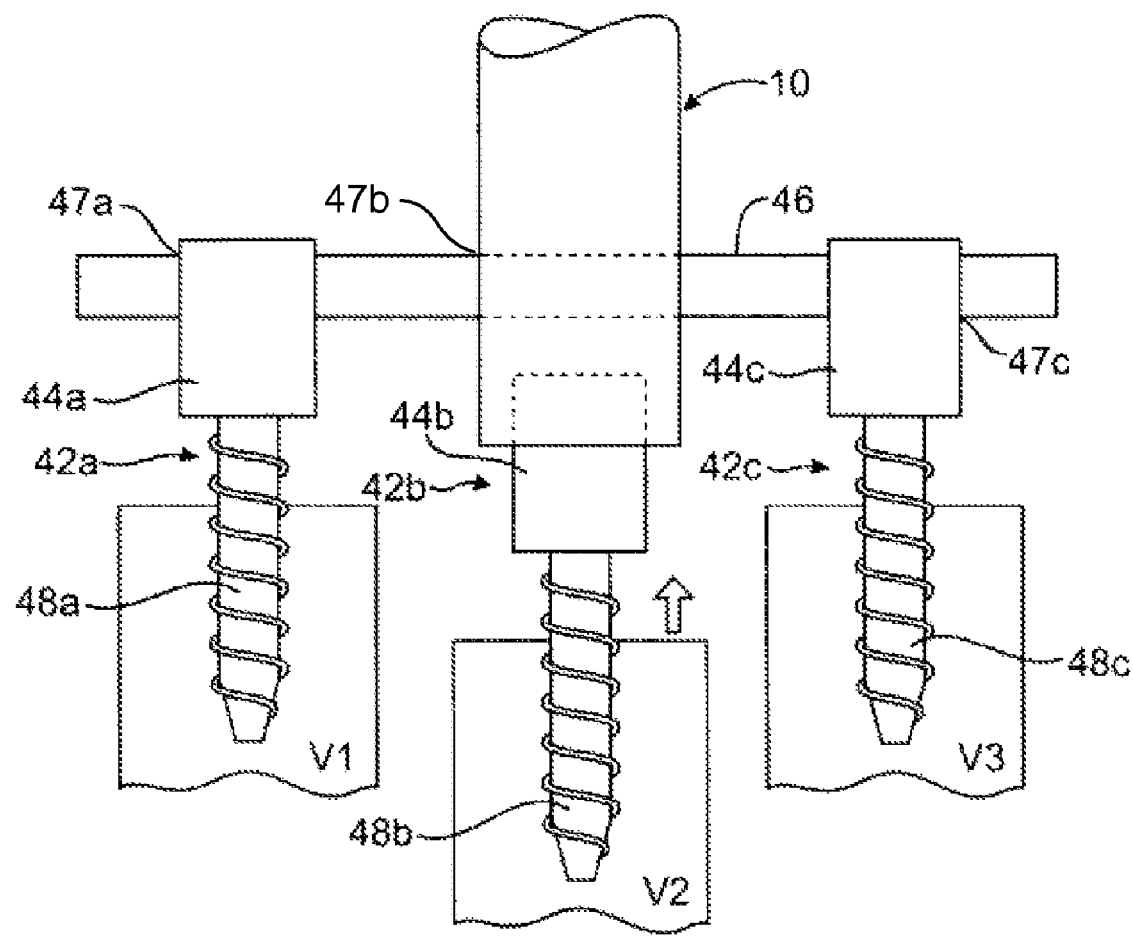
FIG. 3 is a side view of three bone screw systems implanted into three respective vertebral bodies, a rod interconnecting the three bone screw systems and rod reduction instrument connected to the middle bone screw system.

There is shown in FIG. 3 a multi-level application of three bone screw systems 42a, 42b, 42c installed into vertebrae V1, V2 and V3, respectively, along one side of a patient's spine. Each bone screw system 42a, 42b, 42c includes a seat 44a, 44b, 44c that allows a rod 46 to be positioned within a seat rod channels 47a, 47b, 47c and secured to bone screws 48a, 48b, 48c. In one variation of the seat, the seat includes parallel flat portions on the outer surface of the seat. In order to facilitate the surgeon's positioning of the rod 46 in all of the seats 44a, 44b, 44c of screw systems 42a, 42b, 42c, the rod reducer instrument 10 is engageable to the seat and as shown in FIG. 3 in particular, the rod reducer instrument 10 is engageable to middle seat 44b to reduce the distance between the seat 44b and the rod 46 as the condition of the spine has slightly displaced the middle vertebra V2 making it difficult seat the 46 into the middle seat 44b. Hence, the rod reducer instrument is positioned against the rod 46 and thereafter operable to move the rod 46 and the seat 44b into closer proximity to each other in a manner that draws vertebra V2 in the direction of the arrow in FIG. 3 such that the rod 46 is positioned within the channel 47b, inside the seat 44b and capable of being secured thereto with a locking mechanism such as a cap and/or set screw combination (not shown). Various bone screw systems that employ polyaxial or uni-axial screws are within the scope of the present invention as well as non-screw fastening systems such as hooks and other bone or tissue engaging devices.

The rod 46 is typically an elongated substantially cylindrical member that is straight or curved, however the invention is not so limited and a rod having any size or shape is within the scope of the invention so long as it can be secured to the seat 44 of the bone screw system 42 and serves its stabilizing function.

Figure 4:
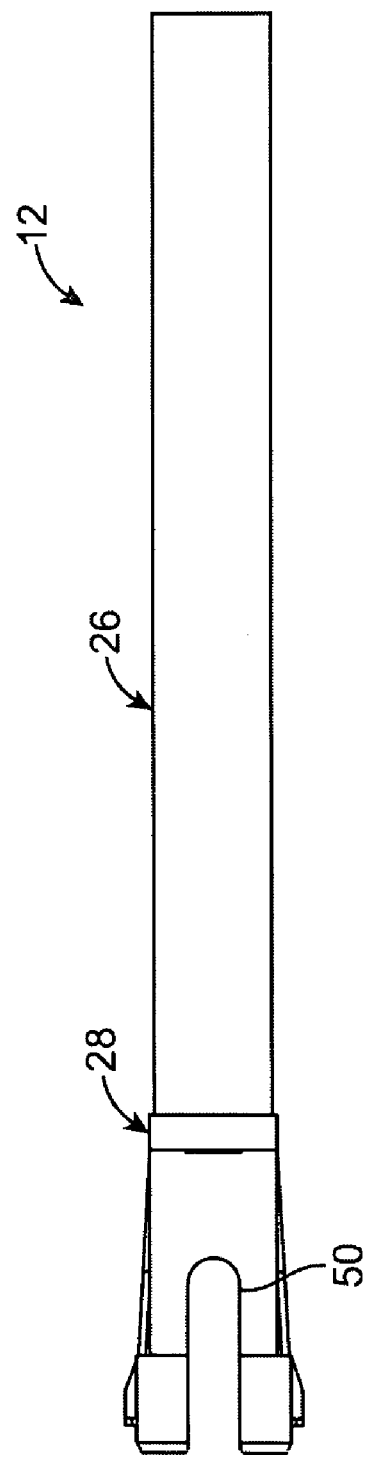
FIG. 4 is a side elevational view of the cannula assembly of the rod reduction instrument according to the present invention.

The cannula assembly 12 will now be described. With reference to FIG. 4, there is shown a side elevational view of the cannula assembly 12. The cannula assembly comprises an inner cannula 26 connected to a seat clamp 28.

Figure 5:
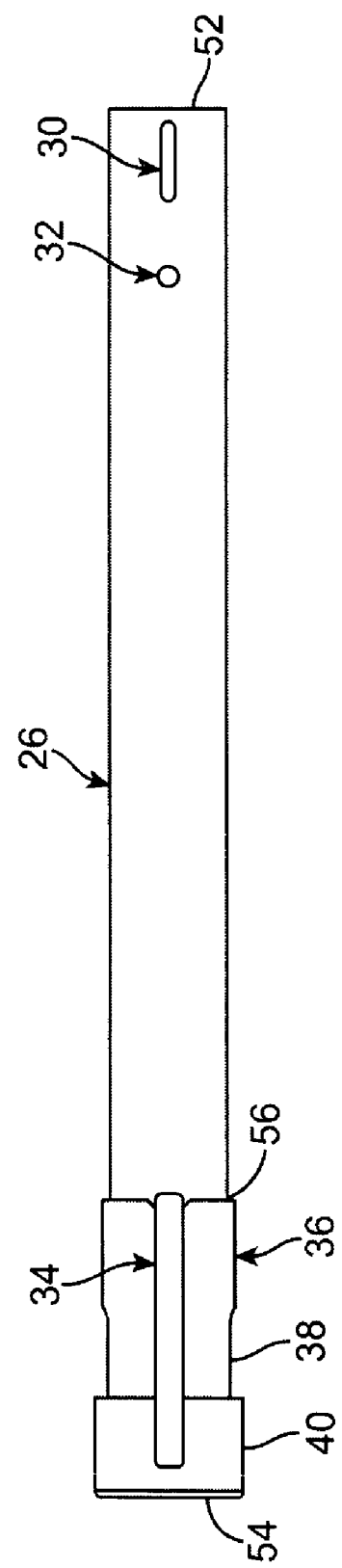
FIG. 5 is a top view of the cannula according to the present invention.

A top view of the inner cannula 26 is shown in FIG. 5. The cannula 26 is generally cylindrically shaped and has a first end 52 and a second end 54. A central inner bore 60 (visible in FIG. 6A) is formed between the first end 52 and the second end 54. The cannula 26 includes a retaining slot 30, a pin hole 32 and a "finger" slot 34 all formed in the cannula 26 along a central longitudinal cross-sectional plane. A second "finger" slot 34 that is not visible in FIG. 5 is included on the cannula 26 in a location directly opposite from the first finger slot 34.

Referring back to FIG. 4, the cannula also includes a cannula rod channel 50 formed at the distal end of the cannula 26. The cannula rod channel 50 is formed in a longitudinal plane that is substantially perpendicular to the longitudinal plane along which the retaining slot 30 and pin hole 32 are formed. A second cannula rod channel 50 that is not visible in FIG. 4 is formed in a location directly opposite from the first cannula rod channel 50.

Turning back to FIG. 5, the cannula 26 further includes a shoulder 36, a neck 38 and head 40. The neck 38 is interconnected between the shoulder 36 and the head 40 and has a reduced outer cross-sectional diameter along at least a portion of the neck 38 relative to the shoulder 36 and head 40. The shoulder 36 forms an abutment 56 at a proximal end of the shoulder 36 and the head 40 is located distally at the second end 54 of the cannula 26.

Now referring to FIGS. 6A, 6B and 6C, there is shown a cross-sectional view and two end views, respectively, of the cannula 26 according to the present invention with the bore 60 of the cannula 26 being clearly visible. In one variation, the bore 60 includes two longitudinally extending bore channels 62 located directly opposite to each other extending along the length of the cannula 26 between the first and second ends 52, 54. The cannula bore channels 62 are parallel to and in substantial alignment with the rod channels 50.

Figure 6:
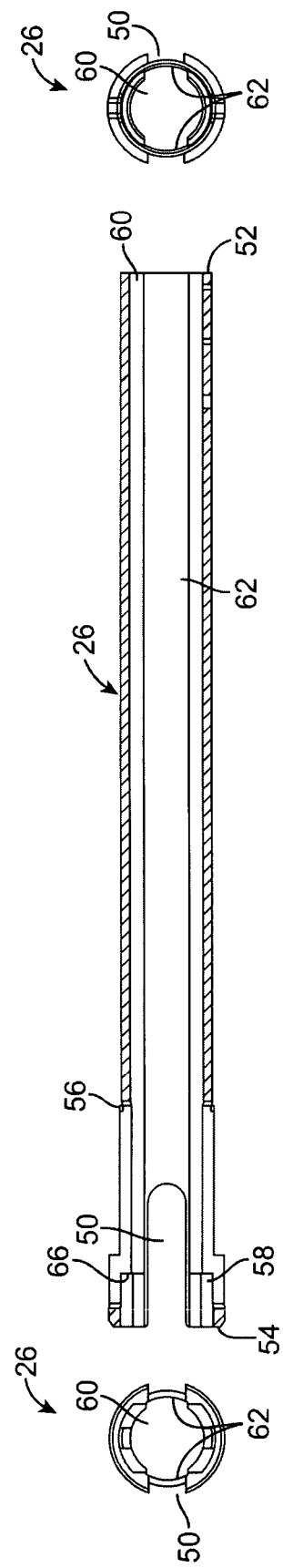
FIG. 6A is a cross-sectional view of the cannula according to the present invention.
FIG. 6B is a distal end view of the cannula according to the present invention.
FIG. 6C is a proximal end view of the cannula according to the present invention.

As seen in FIG. 6A, the inner diameter of the cannula 26 is substantially the same along the neck 38, shoulder 36 and proximal portions of the cannula 26. Also, as seen in FIG. 6, the interior diameter along at least a portion of the head 40 of the cannula 26 is greater relative to the rest of the interior of the cannula 26. This portion along the head 40 with a greater inner diameter defines a seat receiving portion 58. Generally, the seat receiving portion 58 is interconnected with and opens to the second end 54 of the cannula 26. A ledge 66 on the interior surface serves as a stop against which the inserted seat 44 abuts. The seat receiving portion 58 is configured to conform to the shape and size of a seat 44 of a bone screw system 42 and to receive at least a portion of the seat 44 inside the seat receiving portion 58.

Figure 7:
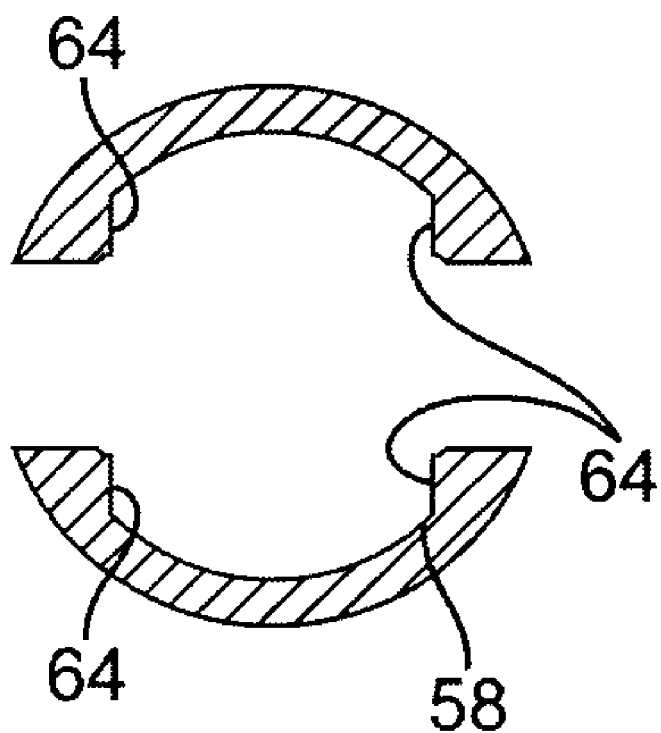
FIG. 7 is a cross sectional view of the seat receiving portion of the cannula according to the present invention.

FIG. 7 shows a cross-sectional area of the seat receiving portion 58. As seen in FIG. 7, the seat receiving portion 58 includes parallel flat portions 64 formed on the inner surface of the seat receiving portion 58. These flat portions 64 match flat portions 49 on a seat 44 of a bone screw system 42. When the seat receiving portion 58 engages a seat 44, the flat portions 64 of the seat receiving portion 58 line up with the flat portions 49 of the seat 44, thereby, properly orienting the seat 44 to the cannula 26 so that the seat 44 can be inserted into the seat receiving portion 58 of the cannula. In this orientation, the seat rod channels 47 advantageously line up with the rod channels 50 in the cannula 26 interconnecting the seat rod channels 47 with the cannula rod channels 50 for placement of the rod 46 into the seat rod channel 47. Also, in this orientation, the cannula bore channels 62 are advantageously lined up and interconnected with the seat rod channels 47 such as for advantageously translating a cap or set screw down the length of the cannula 26 in an orientation that is in alignment with the seat 44 for connecting thereto to lock the rod 46 inside the seat rod channel 47.

Figure 8:
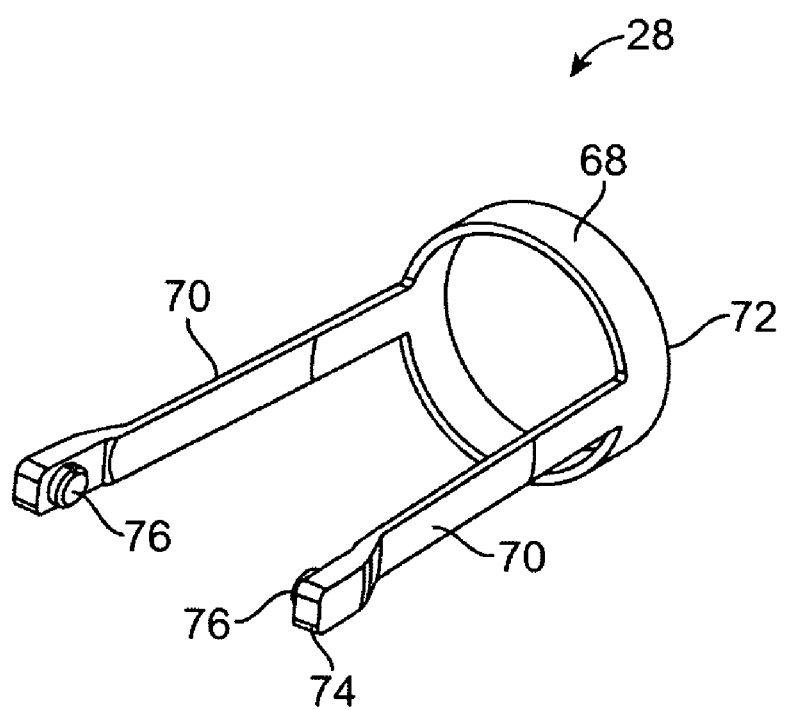
FIG. 8 is perspective view of the seat clamp of the cannula assembly according to the present invention.

Turning now to FIG. 8, there is shown a seat clamp 28 having a proximal end 72 and a distal end 74 according to the present invention. The seat clamp 28 includes a base 68 and two substantially parallel fingers 70 extending longitudinally from the base 68. The base 68 is ring-shaped having an inner diameter that is slightly larger than the outer diameter of the proximal portion of the cannula 26 yet smaller than the outer diameter of the shoulder portion 36 such that seat clamp 28 contacts the abutment 56 at the ring 68. At the distal end 74 of each finger 70, an inwardly extending nib 76 is formed. Each nib 76 is configured to mate with corresponding recesses formed on the seat 44 of a bone screw system. Other mating configurations are discussed in reference to FIGS. 24A, 24B, 24C and 24D.

Figure 9:
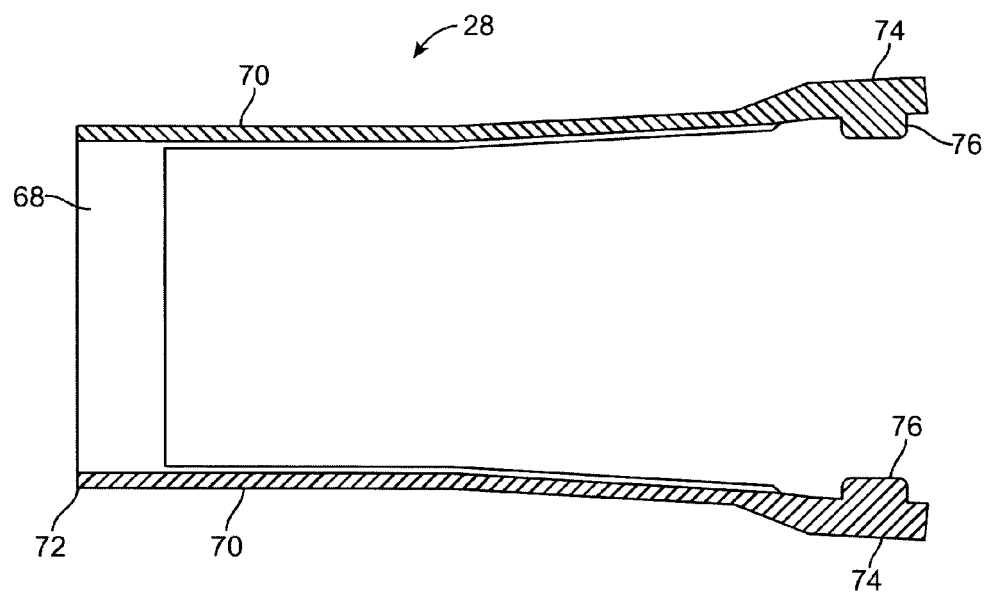
FIG. 9 is a cross-sectional view the seat clamp of the present invention.

FIG. 9 illustrates a cross-sectional view taken longitudinally through the fingers 70 of the seat clamp 28. As seen in FIG. 9, the fingers 70 are angled slightly outwardly to create a leaf spring exerting an outward spring force when the distal ends 74 are pushed together as will be evident and described hereinbelow.

To assemble the cannula assembly 12, the cannula 26 and seat clamp 28 are oriented such that the distal end 74 of the seat clamp 28 and the distal end 54 of the cannula 26 are lined up and the ring-shaped base 68 of the seat clamp 28 is passed over the proximal end 52 of the cannula 26 until the base 68 contacts the shoulder abutment 56. The seat clamp 28 is rotated to align the two fingers 70 with the two finger slots 34 such that the fingers 70 are allowed to flex into the finger slots 34.

Figure 10:
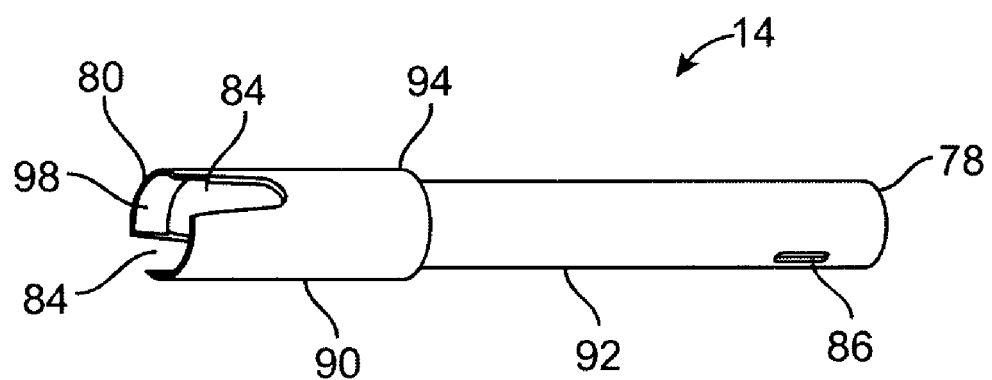
FIG. 10 is a perspective view of the locking shaft according to the present invention.
Figure 11:
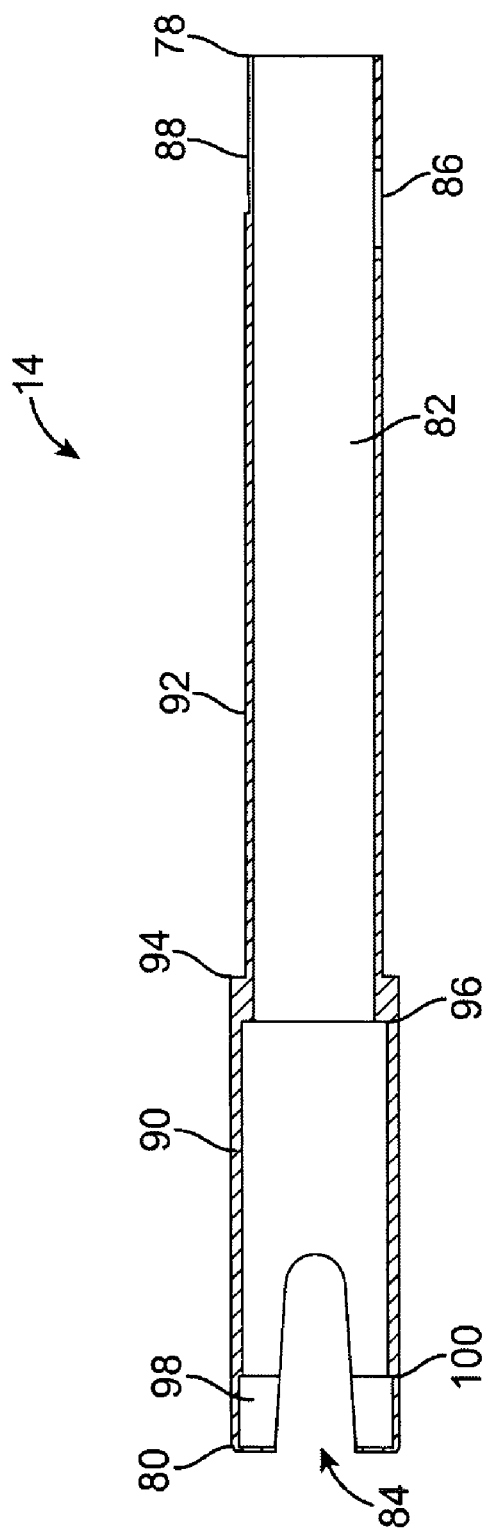
FIG. 11 is a cross-sectional view of the locking shaft according to the present invention.

With reference to FIGS. 10 and 11, the locking shaft or middle cannula 14 will now be described. FIG. 10 shows a perspective view of the locking shaft 14 and FIG. 11 shows a cross-sectional view. The locking shaft 14 is generally cylindrically shaped and has a proximal end 78 and a distal end 80 and a central inner bore 82 extending between the proximal end 78 and the distal end 80. A pair of rod channels 84 opposite from one another is formed in the locking shaft 14 at the distal end 80. Each rod channel 84 extends longitudinally and opens at the distal end 80. A pin through slot 86 is formed near the proximal end 78 of the locking shaft 14. The proximal end 78 includes a flat portion 88 on the outer surface of the locking shaft 14 for insertion into the body assembly 18 and for preventing rotation with respect to the body assembly 18.

Still referencing FIGS. 10 and 11 and with particular reference to FIG. 11, the locking shaft 14 includes a head portion 90 and a shaft portion 92. As seen in FIG. 11, the head portion 90 has an outer diameter that is larger than the outer diameter of the shaft portion 92 with an outer locking shaft abutment 94 formed at the intersection of the head portion 90 and shaft portion 92 for biasing a first spring (not shown).

Turning now to the inside of the locking shaft 14, the inner diameter of the shaft portion 92 is smaller than the inner diameter of the head portion 90. An inner locking shaft abutment 96 is formed inside at the intersection of the shaft portion 92 and the head portion 90 for biasing a second spring (not shown). The inner locking shaft abutment 96 is located distally relative to the outer locking shaft abutment 94. The head portion 90 further includes a cannula head receiving portion 98 that has an inner diameter that is larger than the inner diameter of the rest of the head portion 90. An inner cannula head abutment 100 is formed inside at the intersection of the cannula head receiving portion 98 of the head portion 90 and the rest of the head portion 90.

Figure 12:
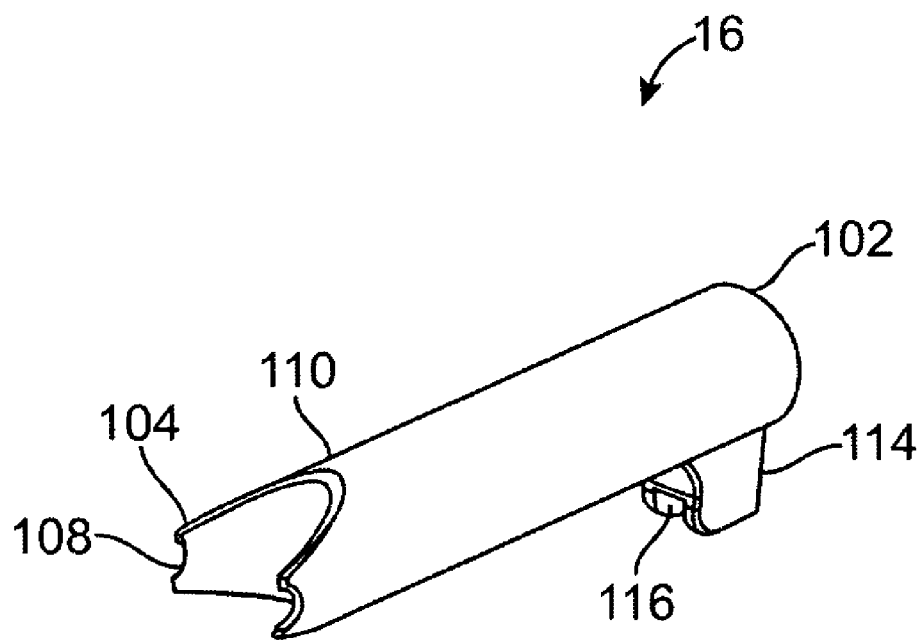
FIG. 12 is a perspective view of the plunger according to the present invention.
Figure 13:
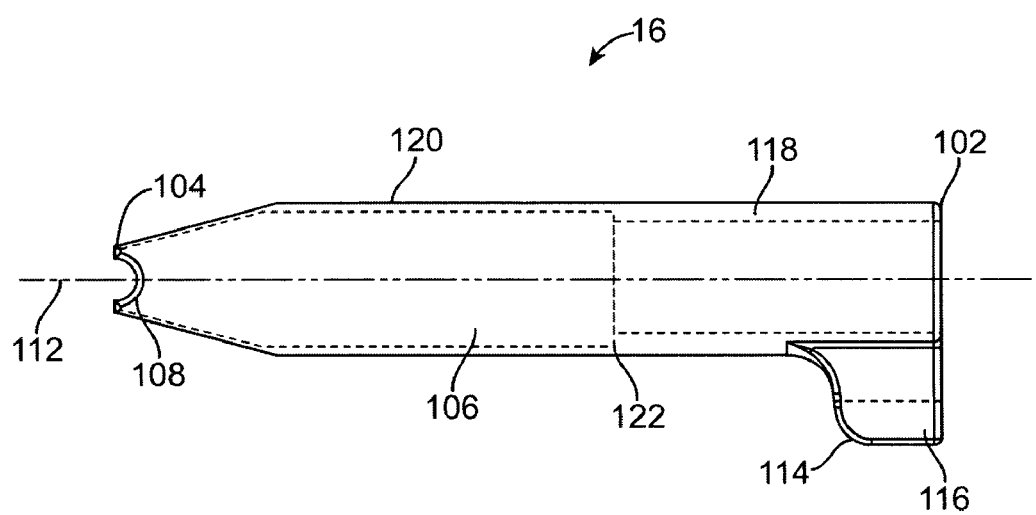
FIG. 13 is a side elevational view of the plunger according to the present invention.

With reference to FIGS. 12 and 13, the plunger or outer cannula 16 will now be described. The plunger 16 is generally cylindrically shaped and has a proximal end 102 and a distal end 104. A central plunger bore 106 extends between the proximal end 102 and the distal end 104. The pair of corresponding rod engaging surfaces 108 are formed at the distal end 104 and positioned opposite from each other. Also formed at the distal end 104, are a pair of scalloped portions 10 (FIG. 12). The scalloped portions 110 interconnect with the pair of rod engaging surfaces 108 such that the side profile of the plunger 16 is angled towards the plunger's central longitudinal axis 112 as seen in FIG. 13. The plunger 16 further includes a rack connecting portion 114 integrally formed or connected to the outer surface of the plunger 16 for connecting to a rack as will be described below. The rack connecting portion 114 includes a rack receiving channel 116.

Turning now to the inside of the plunger 16 and referencing FIG. 13 in particular, the inside of the plunger 16 is divided into a proximal section 118 and a distal section 120. The proximal section 118 is characterized by an inner diameter that is smaller than the inner diameter of the distal section 120 of the plunger 16. The intersection of the proximal section 118 with the distal section 120 forms an inner plunger abutment 122 for biasing the first spring (not shown).

The body assembly 18 will now be discussed. The body assembly 18 includes a body 124, a plunger driver 126 connected to the body 124 and a cannula spring lock system 128 connected to the body 124.

Figure 14:
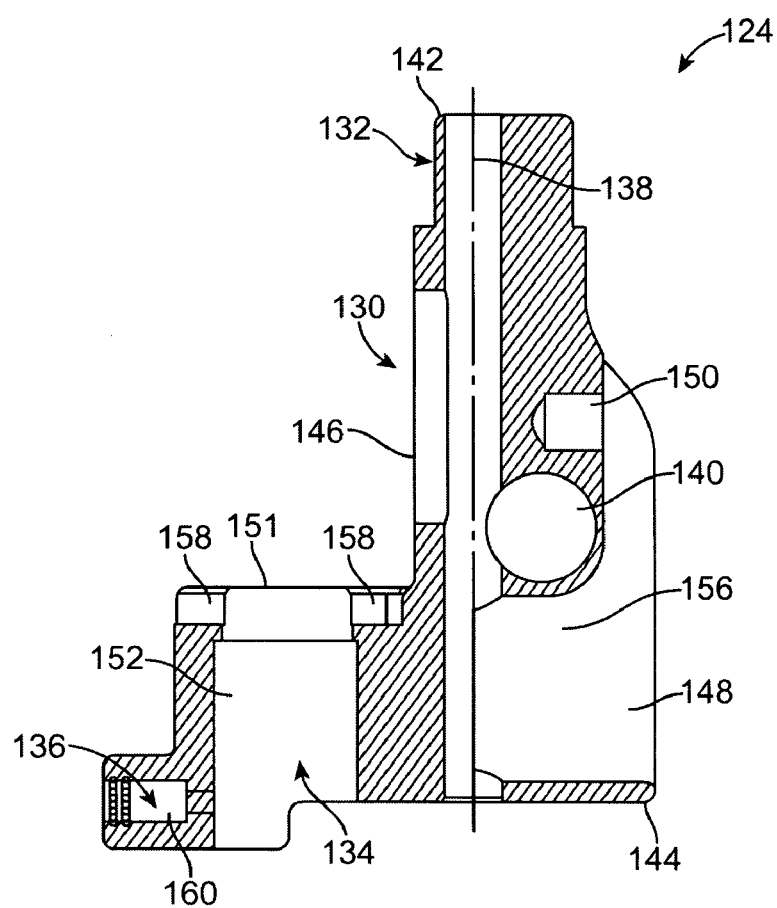
FIG. 14 is a cross-sectional view of the body according to the present invention.

Referring now to FIG. 14, there is shown a cross-sectional view of the body 124 having a proximal end 142 and a distal end 144. The body 124 includes a plunger driver receiving portion 130, a handle connecting portion 132, a locking shaft receiving portion 134 and a cannula spring lock system receiving portion 136.

Still referencing FIG. 14, the plunger driver receiving portion 130 is configured to receive a plunger driver 126. The plunger driver 126 can be selected from any number of mechanical driving systems. In one variation of the invention, the plunger driver 126 is a rack and pinion system. Therefore, the plunger driver receiving portion 130 of the body 124 is configured to receive a rack and pinion system. To that end, the plunger driver receiving portion 130 includes a rack passageway 138 and a pinion receiving aperture 140. The rack passageway 138 extends between the proximal end 142 and the distal end 144. The pinion receiving aperture 140 is interconnected with the rack passageway 138 as shown in FIG. 14. In one variation, the body 124 includes a rack viewing window 146 for viewing the position of the rack with respect to the body that will be discussed in greater detail below with respect to FIG. 25. In one variation of the invention, the rack and pinion system includes a rack lock to arrest retraction of a spring biased rack. To that end, the body 124 further includes a rack lock receiving portion 148 and a rack lock spring receiving portion 150 that houses a spring to bias a trigger. A pin hole 156 for connecting a trigger of the rack lock is formed in the body 124 and interconnected with the rack lock receiving portion 148.

Still referencing FIG. 14, the handle connecting portion 132 of the body 124 includes a reduced cross-sectional portion of the body at the proximal end 142 for connecting with the handle 22 via a handle connector 24. In one variation, the handle 22 is integrally formed with the body 124 and there is no need for a reduced cross-sectional portion of the body.

Still referencing FIG. 14, the locking shaft receiving portion 134 of the body includes a bore 152 sized slightly larger than the outer diameter of the locking shaft 14 to provide for a tight compression fit engagement with the body 124. In one variation, the bore 152 extends from one end of the body to the other forming an opening 151 towards proximal end of the body. The opening 151 of the bore 152 opens at the surface of the body 124 to provide access to inside the bore 152. The body 124 also includes a locking pin aperture 154 (visible in FIG. 1) that is interconnected with the bore 152 for receiving a pin to help lock the locking shaft 14 and cannula assembly 12 in place. A flat portion (not shown) is formed inside the bore 152 such that it corresponds to the flat portion 88 of the locking shaft 14 for aligning the locking shaft 14 inside the bore 152 and for preventing rotation of the locking shaft 14 inside the bore 152 relative to the body. In one variation, locking mechanism inserter notches 158 are formed in the body at the proximal end of the bore 152 for connecting with and orienting a locking mechanism inserter instrument with respect to the body.

Still referencing FIG. 14, a cannula spring lock system receiving portion 136 includes an aperture 160 extending between the bore 152 and the outer surface of the body 124 for receiving a cannula spring lock pin.

Figure 15:
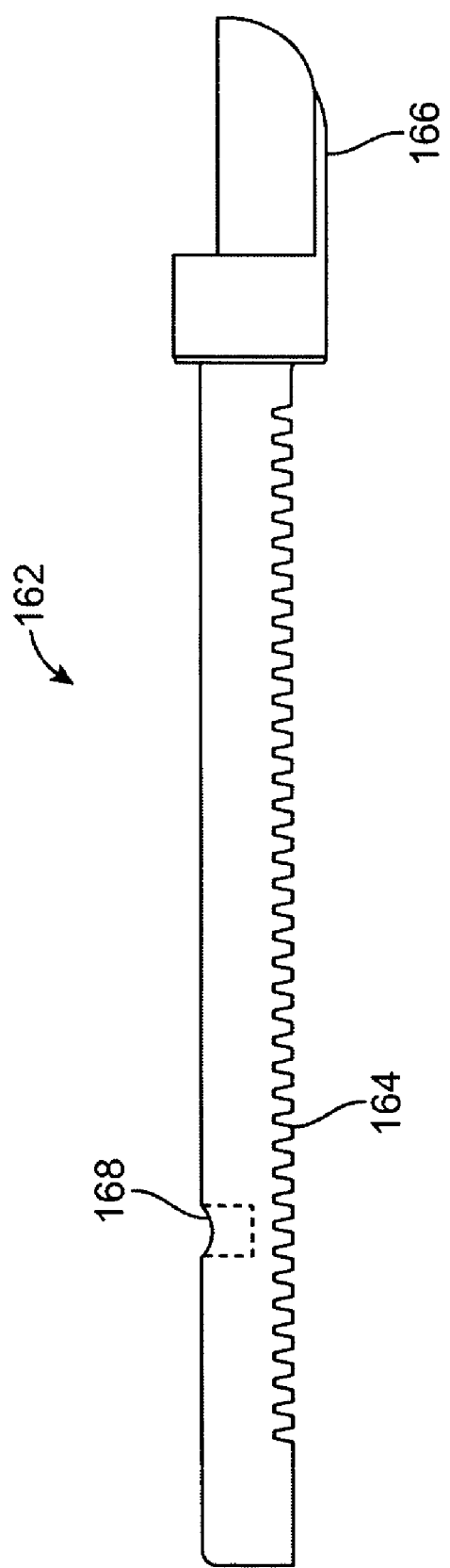
FIG. 15 is a side elevational view of the rack of the rack and pinion system according to the present invention.

Turning now to FIG. 15, there is shown a side-elevational view of a rack 162 of the rack and pinion system 126. The rack 162 includes an elongated element having teeth 164 and a connecting portion 166 configured to connect to the rack connecting portion 114 of the plunger. The rack 162 is configured to be located in the rack passageway 138. In one variation, the rack 162 includes an indicator 168 that can be a mark, protrusion or any kind of indicator located and configured to be visible through the rack viewing window 146.

Figure 16:
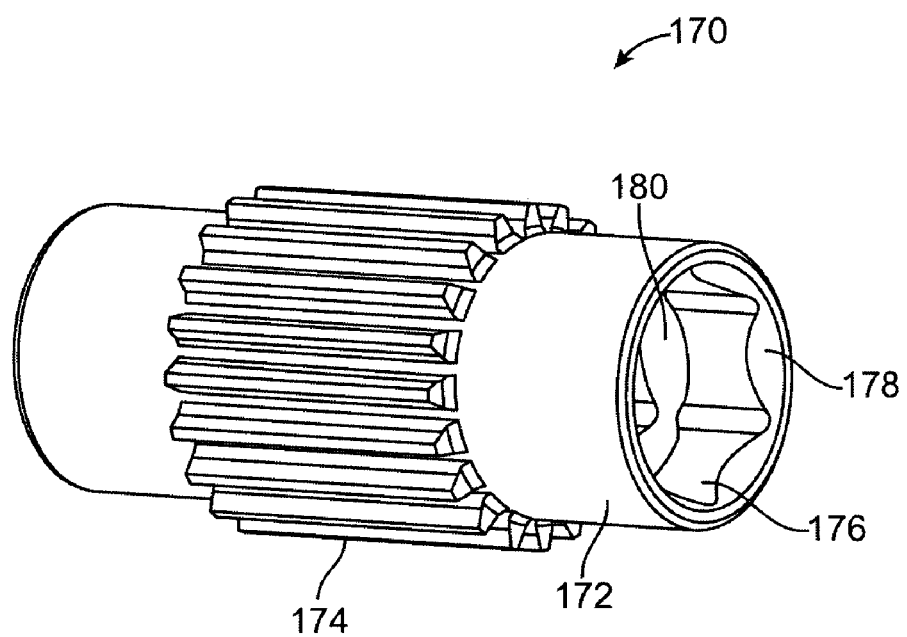
FIG. 16 is a perspective view of the pinion of the rack and pinion system according to the present invention.
Figure 17:
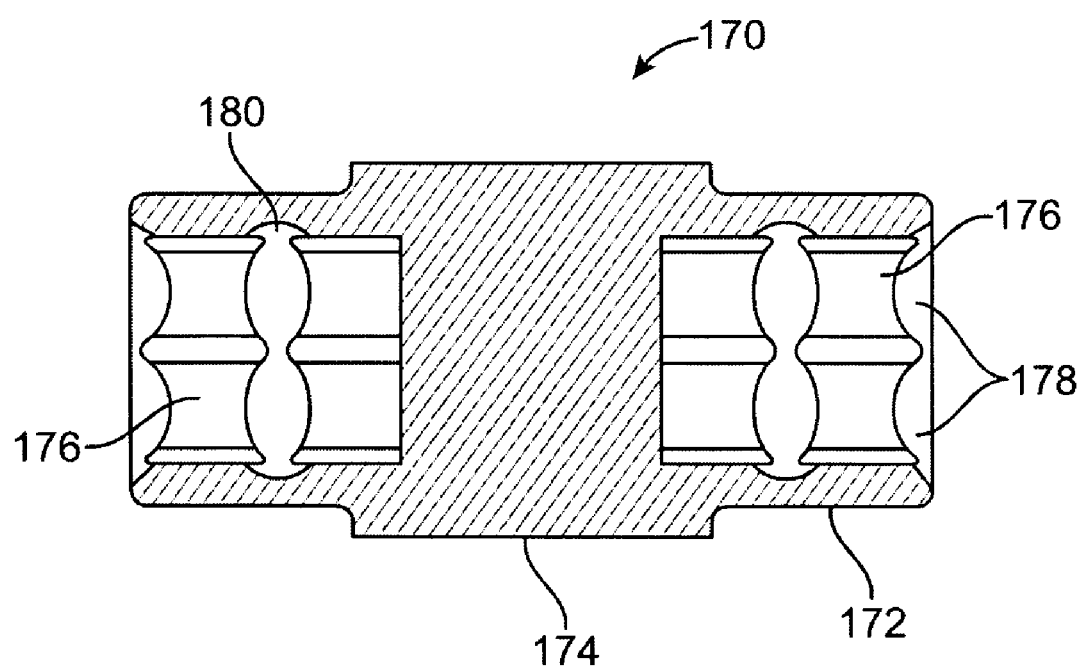
FIG. 17 is a cross-sectional view of the pinion of FIG. 16 according to the present invention.

Referring now to FIGS. 16 and 17, there is shown a perspective view of a pinion 170 of the rack and pinion system 126. The pinion 170 includes an axle 172 and a geared portion 174. In one variation, the gear portion 174 includes a plurality of teeth and is centrally located along the pinion 170 as shown in FIGS. 16 and 17. In general, the pinion is substantially cylindrical in shape and is configured to be inserted into the pinion receiving aperture 140 of the body 124. In one variation, the pinion 170 includes at least one pinion bore 176 formed inside the pinion 170. In one variation, two pinion bores 176, one at either end of the pinion 170, are formed such that each pinion bore 176 opens at the surface of each end of the pinion 170 as shown in FIG. 17. Alternatively, a single pinion bore 176 extends end-to-end inside the pinion 170. As seen in FIG. 16, the inner surface of the at least one pinion bore 176 is substantially hexagonal in shape configured to receive therein a hexagonal member. Although the inner surface is hexagonal, the invention is not so limited and the inner surface can be any shape. The rim of the pinion bore 176 includes lead-in ramps 178 for guiding and facilitating insertion of a hexagonal member into the pinion bore 176. The inner surface of the pinion bore 176 includes a locking groove 180 configured to receive a locking member therein.

Figure 18:
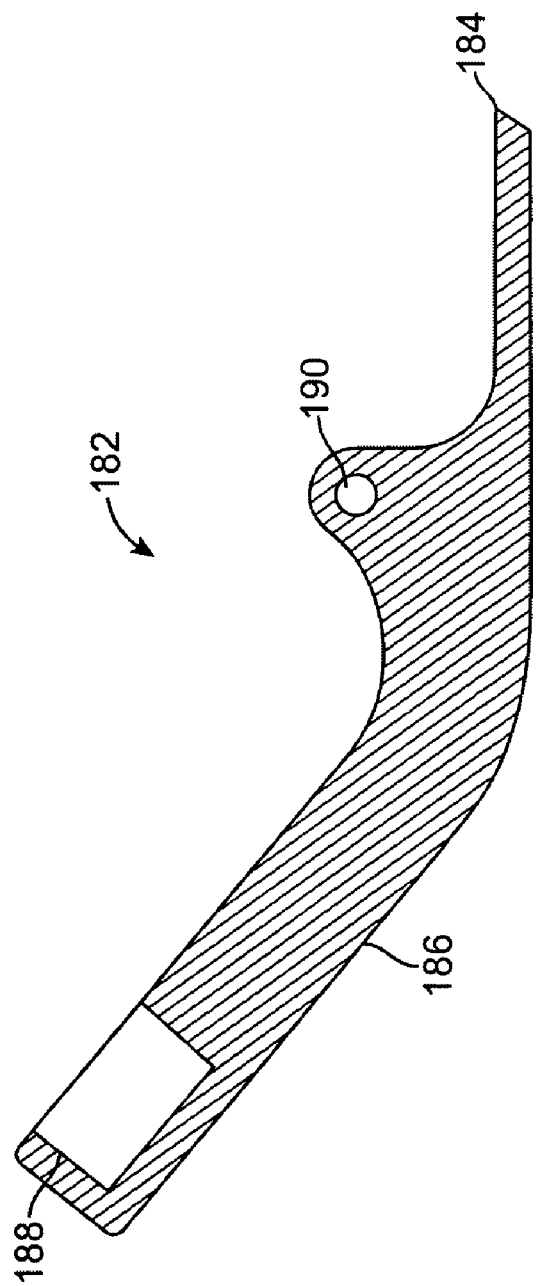
FIG. 18 is a cross-sectional view of a trigger according to the present invention.

Referring now to FIG. 18, there is shown a cross-sectional view of a trigger 182 of a rack lock. The trigger 182 is angled and includes a rack engaging end 184 configured to engage the teeth of the rack 162. The trigger 182 also includes a finger receiving portion 186. The trigger 182 further includes a spring receiving portion 188 configured to receive a spring therein. In one variation, the spring receiving portion 188 is a well located at the proximal end of the finger receiving portion 186. The trigger 182 further includes a pin hole 190 configured to receive a pin, attach the trigger 182 to the body 124 and serve as a pivot point for the trigger 182.

Figure 19:
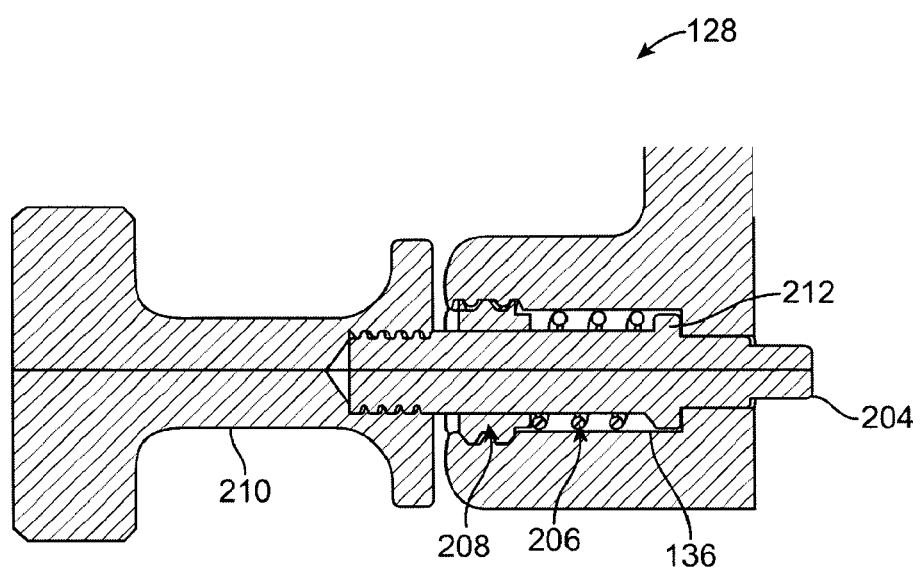
FIG. 19 is a partial cross-sectional view of the body and cross-sectional view of the cannula spring lock system according to the present invention.

Referring now to FIG. 19, the cannula spring lock system 128 will now be described. FIG. 19 is a partial cross-sectional view of the body with a cross-sectional view of the cannula spring lock system 128 disposed inside the cannula spring lock system receiving portion 136 of the body 124. The cannula spring lock system 128 includes a pin 204, spring 206, plug 208 and knob 210. The pin 204 includes a flange stop 212 extending outwardly and configured to abut a ledge inside the cannula spring lock system receiving portion 136 of the body 124. The pin 204 is disposed inside the receiving portion 136. The spring 206 is inserted onto the pin 204 and the plug 208 is threaded into the receiving portion 136 to contain the spring 206 between the flange stop 212 and the plug 208 such that a spring force is generated to bias the pin 204 into the pin hole 32 of the cannula 26. The pin 204 is connected to the knob 210 via threaded portions on the pin 204 and knob 210.

With reference back to FIG. 1, the handle connector 24 will now be described. In one variation, the handle connector 24 includes a body engaging portion 192, a handle engaging portion 194 and an interconnecting stem 196 connected between the body engaging portion 192 and the handle engaging portion 194. In one variation, the body engaging portion 192 is configured to mate with a corresponding portion of the body 124. For example, a ring-shaped body engaging portion 192 mates with a body portion having a circular cross-section with an outer diameter that is smaller than the inner diameter of the ring-shaped body engaging portion 192 as shown in FIG. 1. The handle engaging portion 194, in one variation, includes a projection having a circular cross-section that mates with a bore in the handle 22 having a circular shape. Although circular cross-sections and shapes have been discussed, the invention is not so limited and cross-sections and shapes of any kind are within the scope of the present invention. In another variation, the handle 22 and handle connector 24 may be integrally formed and in another, the handle 22, handle connector 24 and body 124 may be integrally formed.

Still referring back to FIG. 1, the handle 22 will now be described. The handle 22 is large enough for comfortable gripping by a user and may include surface features that aid in handling of the rod reducer. In one variation, the handle 22 includes a bore inside the handle 22 that opens at one end of the handle and has a shape that is complementary for receiving a handle engaging portion of the handle connector or body.

Figure 20:
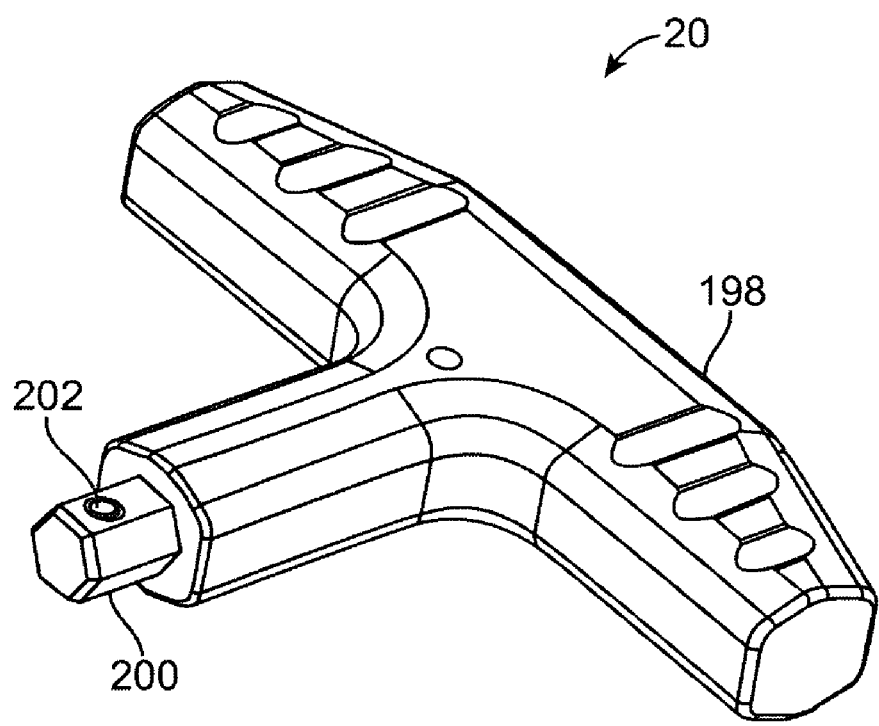
FIG. 20 is a perspective view of a pinion driver according to the present invention.
Figure 21:
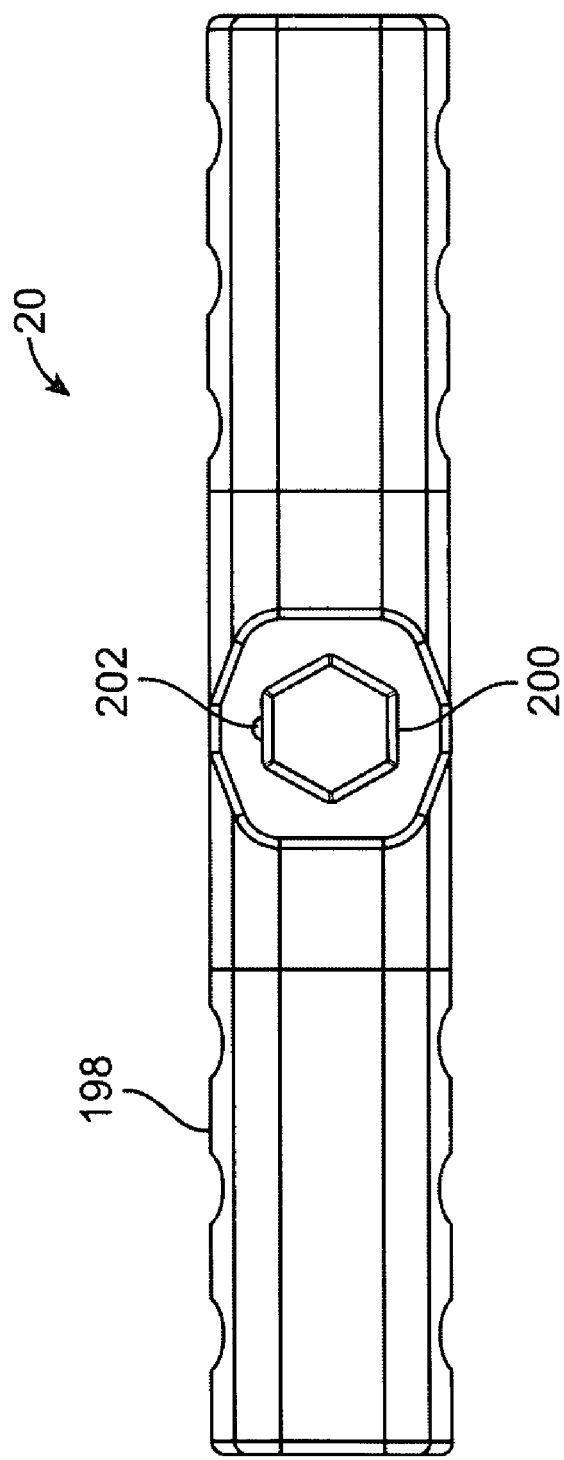
FIG. 21 is an end elevational view of the pinion driver of FIG. 19 according to the present invention.

Referring now to FIG. 20 and FIG. 21, the pinion driver 20 will now be described. FIG. 20 is a perspective view of the pinion driver 20 and FIG. 21 is an end-elevational view of the pinion driver 20. The pinion driver 20 includes a handle portion 198 and a pinion engaging member 200. The pinion driver 20 is generally T-shaped and the handle portion 198 is configured to allow a user to comfortably and firmly grip the pinion driver 20. The pinion engaging member 200 is configured to engage the pinion 170. In one variation, the pinion engaging member 200 is substantially hexagonal in shape to complementarily match a hexagonal-shaped pinion bore 176. The pinion engaging member 200 may be tapered to facilitate insertion into the pinion 170. Although hexagonal-shaped members are described, the invention is not so limited and any functional shape is within the scope of the invention. In one variation of the invention, a ball plunger 202 is contained inside a recess in the pinion engaging member 200. As seen in FIG. 21, the ball plunger 202 extends outwardly from at least one surface of the pinion engaging member 200 and is configured to engage the locking groove 180 inside the pinion bore 176.

Figure 22:
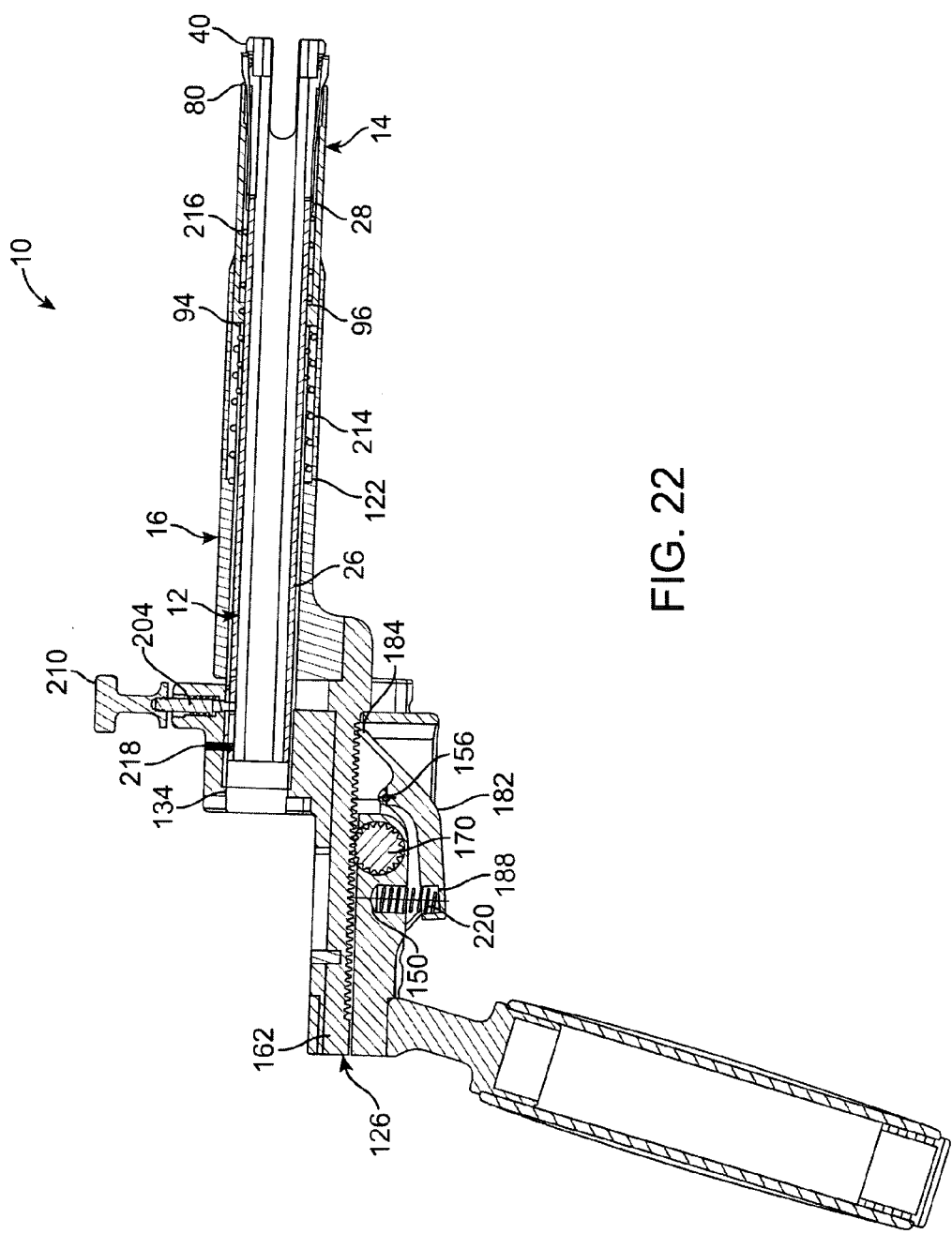
FIG. 22 is a cross-sectional view of the rod reduction instrument of FIG. 2 according to the present invention.

Referring now to FIG. 22, there is shown a cross-sectional view of the rod reducer instrument 10 according to the present invention. The assembly of the instrument 10 will now be discussed in reference to FIG. 22. A first spring 214 is passed over the proximal end 78 of the locking shaft 14 until it is seated against the outer locking shaft abutment 94. The plunger 16 is then passed over the locking shaft 14 such that the first spring 214 is disposed between outer locking shaft abutment 94 and the inner plunger abutment 122. The locking shaft 14, first spring 214 and plunger 16 combination is then connected to the body 124 by first aligning the flat portion 88 of the locking shaft 14 with the flat portion of the bore 152 of the body, inserting the proximal end 78 of the locking shaft 14 into the bore 152 and press-fitting it into the locking shaft receiving portion 134 of the body 124. Additional adhesive material may be employed to secure the locking shaft 14 inside the body 124. The plunger 16 is permitted to move with respect to the locking shaft 14 and is spring biased such that the plunger 16 is forced towards the proximal end of the locking shaft 78 or towards the body 124.

Next, a second spring 216 is inserted in through the distal end 80 of the locking shaft 14. The cannula assembly 12 is then inserted in through the distal end 80 of the locking shaft 14. A pin 218 is passed through the locking pin aperture 154 of the body 124 and through the pin through slot 86 of the locking shaft 14 and into the retaining slot 30 of the cannula 26 to help retain the locking shaft 14. The second spring 216 is retained between the seat clamp 28 and the inner locking shaft abutment 96 such that the second spring 216 is compressed to exert a spring force onto the cannula assembly 12 pushing the cannula assembly 12 in a direction away from the body 124. With the plunger 16 secured, as the cannula 26 is pushed in towards the body from the distal end, the pin 204 of the cannula spring lock system 128 pops, as it is spring biased, into the pin hole 32 of the cannula 26 to lock the cannula assembly 12 into position. The knob 210 is pulled to withdraw the pin 204 and release the cannula 26 and the second spring 216 pushes the cannula assembly 12 such that the head 40 protrudes out from the distal end 80 of the locking shaft 14.

Still referencing FIG. 22, the assembly of the plunger driver 126 will now be discussed. In general, the plunger driver 126 is inserted into the plunger driver receiving portion 130 of the body 124. In one variation of the invention in which the plunger driver 126 is a rack and pinion system, the rack 162 is inserted into the rack passageway 138 of the body 124 and connected to the rack connecting portion 114 of the plunger 16 via a pin. The pinion 170 is inserted into the pinion receiving aperture 140 and the geared portion 174 of the pinion 170 is engaged with the teeth 163 of the rack 162. A bushing (not shown) is employed to press fit the pinion 170 inside the body. A third spring 220 is inserted into the rack lock spring receiving portion 150 of the body and into the spring receiving portion 188 of the trigger 182. The trigger 182 is then secured to the body 124 via a pin (not shown) passed through the pinhole 156 of the body 124 and into the pinhole 190 of the trigger 182 such that the rack engaging end 184 of the trigger 182 can pivot and contact the rack 162.

The handle 22 is then connected to the body 124. If a handle connector 24 is employed, the handle connecting portion 132 of the body 124 is passed into the body engaging portion 192 of the connector 24 and the handle engaging portion 194 is inserted into a bore of the handle 22. In one variation, a dynamic handle connector is provided in which the handle connector 24 permits various orientations of the handle 22 to be locked with respect to the body 124 which provides greater comfort and ease of operation for the surgeon.

Figure 23A:
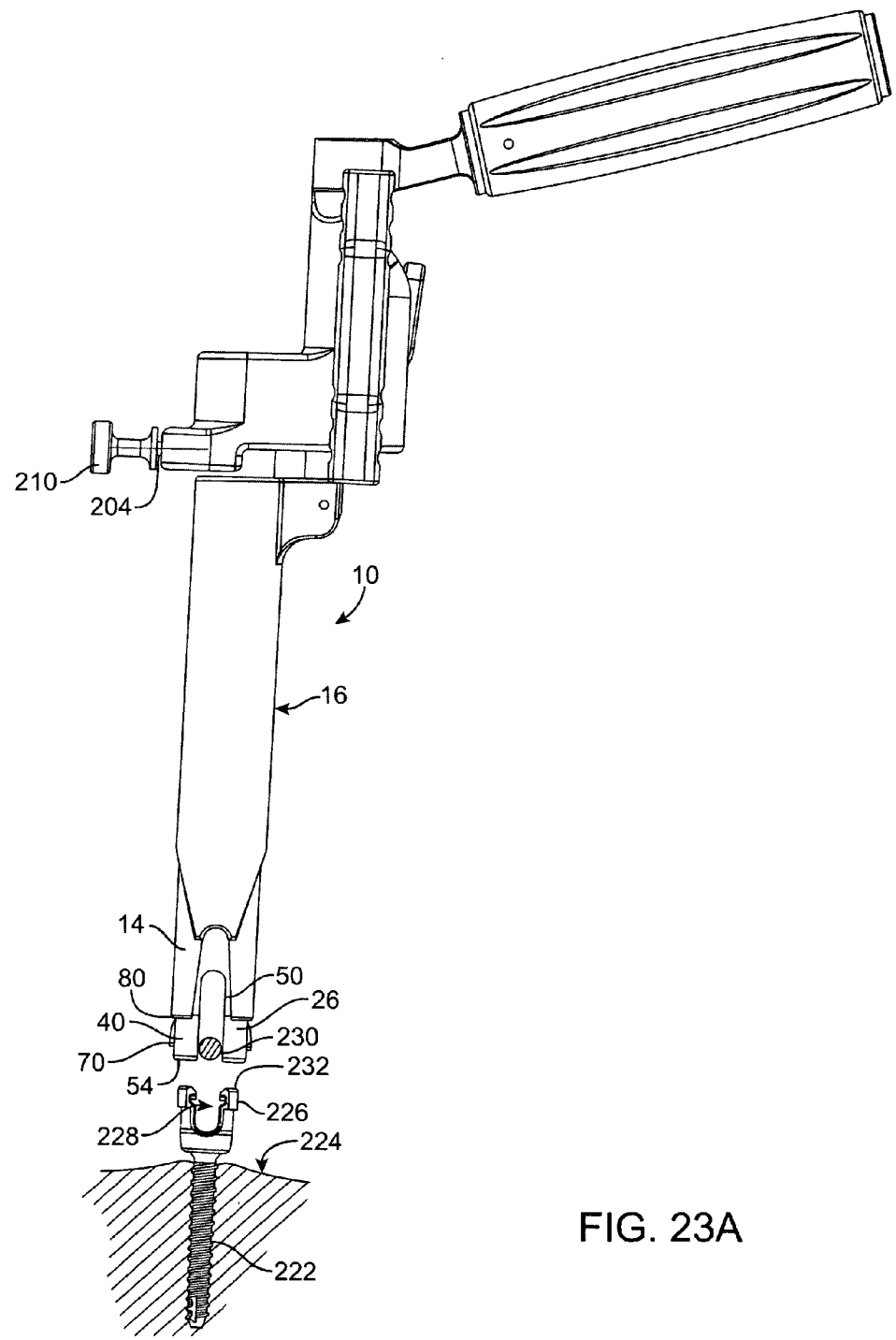
FIG. 23A is a side view of the rod reduction instrument according to the present invention and a bone screw system.
Figure 23B:
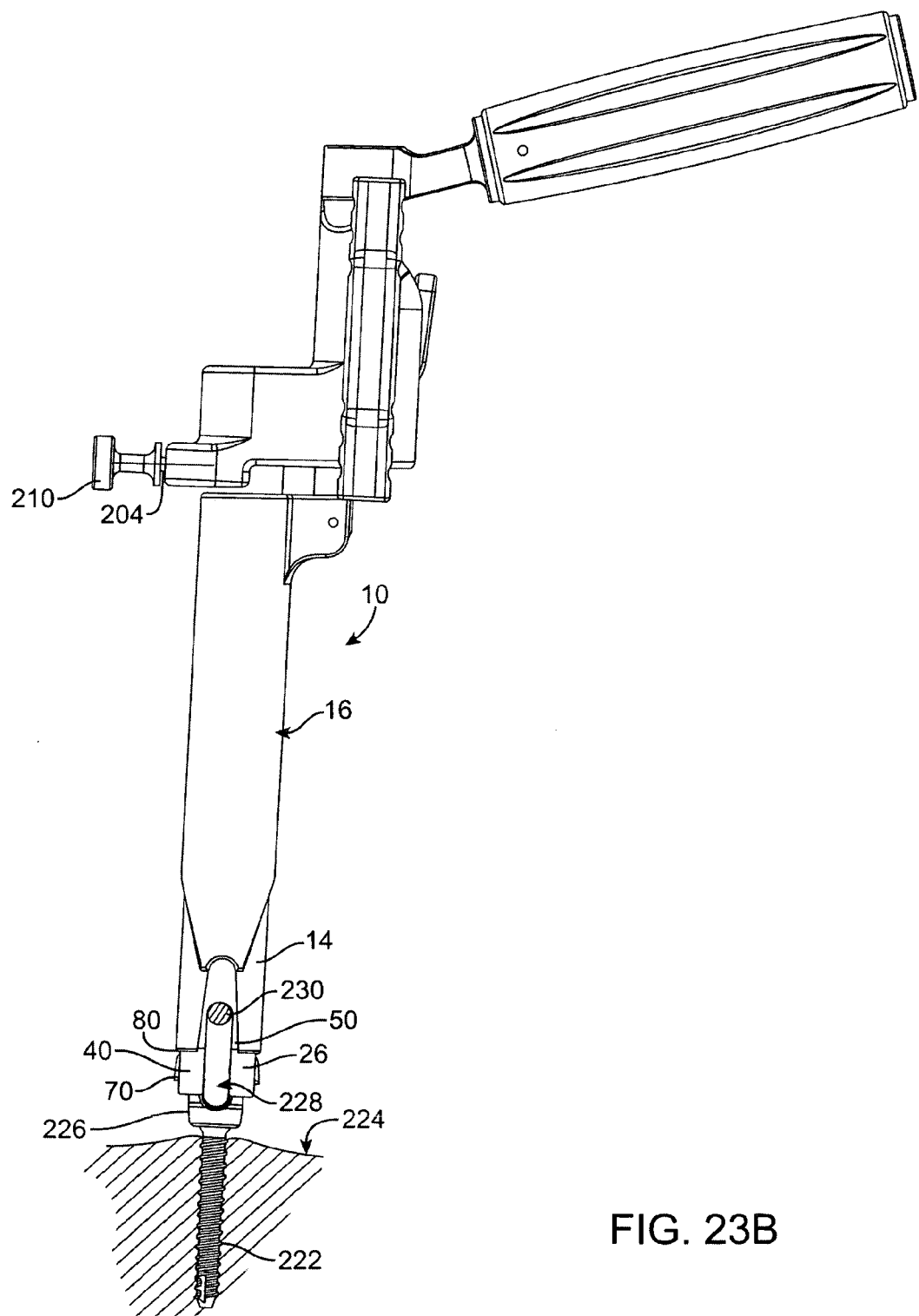
FIG. 23B is a side view of the rod reduction instrument according to the present invention engaging the seat of a bone screw system.
Figure 23C:
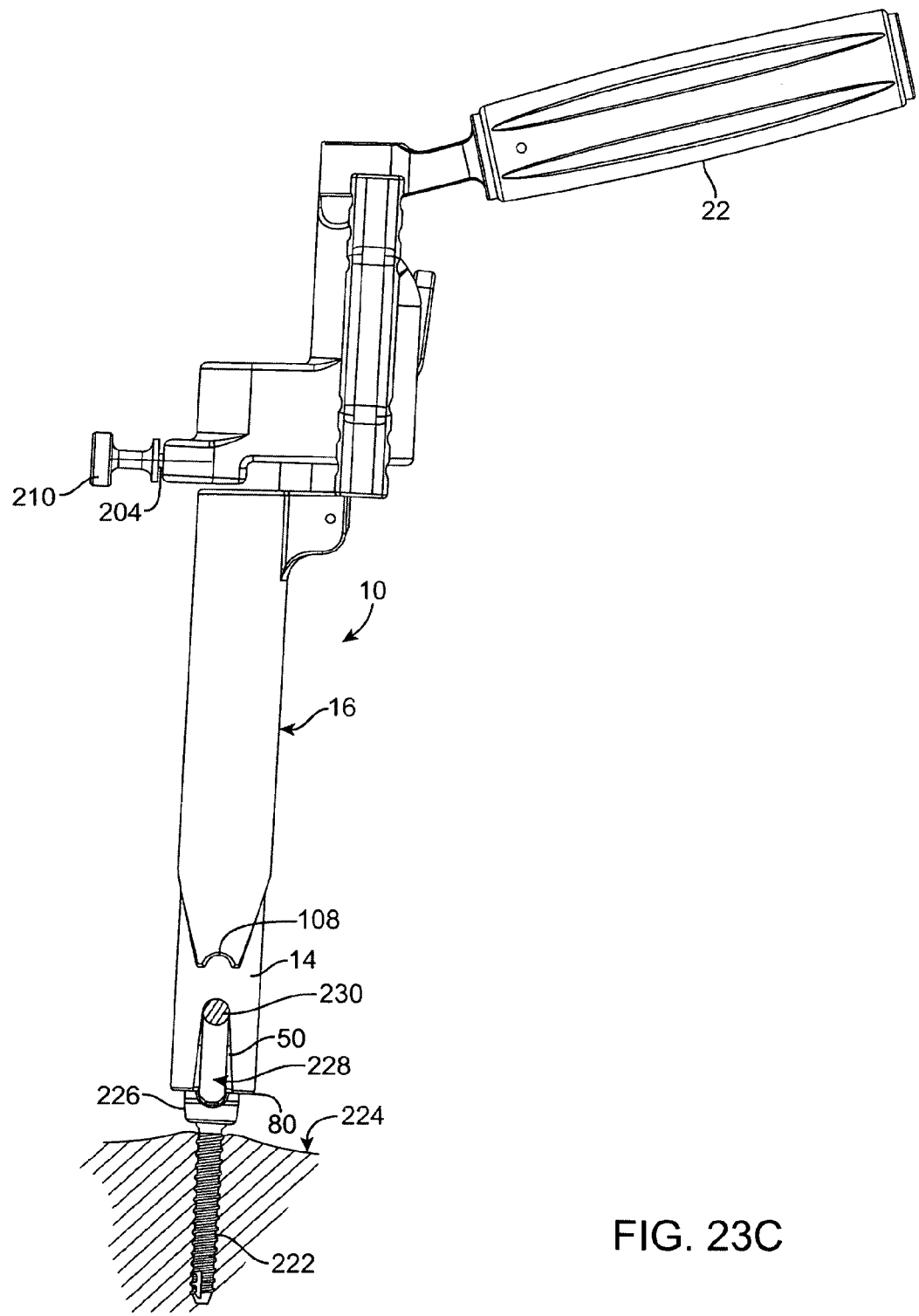
FIG. 23C is a side view of the rod reduction instrument according to the present invention locked onto the seat of a bone screw system.

Referring now to FIGS. 23A-23C, the function of the rod reducer system 10 will now be discussed. The rod reducer 10 is typically employed in open or mini-open or percutaneous minimally invasive operating procedures in which two or more bone screws 222 or fasteners are threaded into a pedicle or other portion of two or more adjacent vertebral bodies. A single bone screw system 222 having a seat 226 with a rod channel 228 deployed in a single vertebral body 224 is shown in FIGS. 23A-23C. Additional bone screw systems 22 deployed in adjacent vertebral bodies are not shown for clarity and these bodies and systems would be located above or below the page. A rod 230 is provided and disposed substantially longitudinally along the length of the spine. A cross-section of a single rod 230 is shown in FIGS. 23A-23C. The rod may be straight or bent to correspond to the normal curvature of the spine in the particular region being instrumented or to such other curvature as the surgeon may deem appropriate to correct the defect. For example, the rod 230 can be bent to form a kyphotic curvature for the thoracic region of the spine, or to form a lordotic curvature for the lumbar region. The rod 230 is engaged to a number of fixation elements fixed to or engaged with the vertebrae along the segment of the spinal column. A variety of fixation elements can be provided that are configured to engage the vertebrae. The bone screw system 222 includes a seat 226 and a rod channel 228 for receiving the rod 230 therein. Affixing the rod 230 to the bone screw system 222 requires the rod 230 to be in close proximity to the bone screw system 222, as shown in FIGS. 23A-23C, or inside the rod channel 228. In some cases, such as in patients with spondylolisthesis where there is an anteroposterior translatory movement of two spinal vertebrae in relation to each other due to instability between the two involved vertebrae, a rod 230 and an implanted screw system 222 must be moved with respect to each other so that the rod 230 is juxtaposed with the seat 266 or occupies the space within the rod channel 228 or other opening in the seat 226 attached to the screw 222 so that the rod 230 can be coupled to the screw 222.

First, as shown in FIG. 23A, the rod reducer 10 is held by the handle 22 and is oriented such that the rod 230 is disposed inside the cannula rod channels 50. The instrument 10 is then advanced such that the rod 230 slides with respect to the rod channels 50 and the distal second end 54 engages the seat 226 such that the seat 226 is received inside the seat receiving portion 58 of the cannula head 40. Flat portions 64 inside the seat receiving portion 58 assist in aligning the instrument 10 with the seat 226. The top 232 of the seat 226 abuts the ledge 66 (shown in FIG. 6A) inside the cannula head 40. This position of the instrument 10 with respect to the seat 226 is shown in FIG. 23B wherein a part of the seat 226 is inside the cannula 26 and hidden from view. In a single action, without the surgeon removing his hand from the handle 22, the surgeon continues to advance the instrument 10 in a direction substantially parallel to the screw 222 into the patient. The continued advancement of the instrument 10 results in the second spring 216 to be further compressed and the distal end 80 of the locking shaft 14 contacts the outer surface of the seat clamp fingers 70 pushing the nibs 76 of the seat clamp 28 into corresponding recesses 234 formed on the outer surface of the seat 226 to lock the seat 226 inside the seat receiving portion 58 of the instrument 10.

Figure 24D:
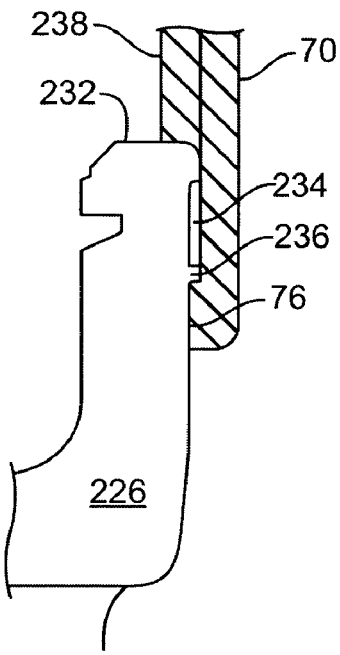
FIG. 24D is a side view of a seat with gripping fingers clamped below the lower flange of the seat and a second portion of the instrument contacting the top surface of the seat according to the present invention.
Figure 24A:
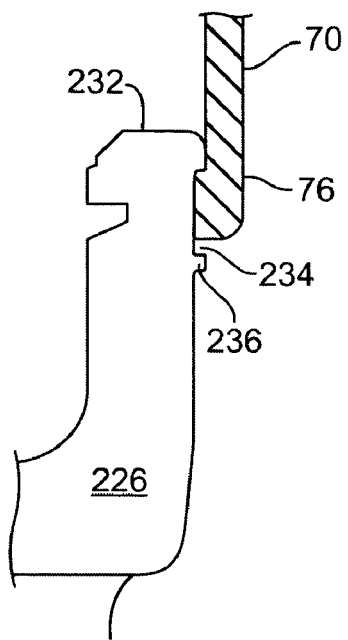
FIG. 24A is a side view of a seat with gripping fingers inserted into the recesses of the seat according to the present invention.
Figure 24C:
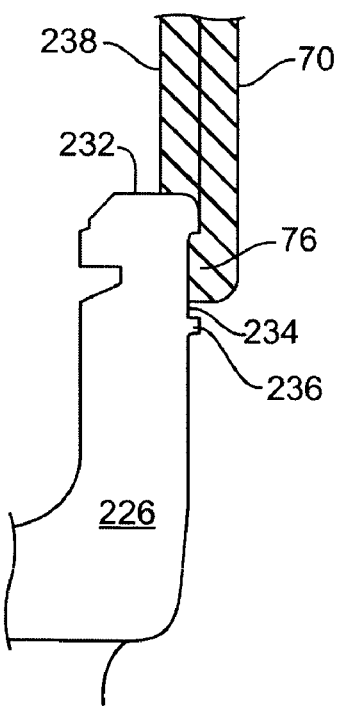
FIG. 24C is a side view of a seat with gripping fingers inserted into the recesses of the seat and a second portion of the instrument contacting the top surface of the seat according to the present invention.
Figure 24B:
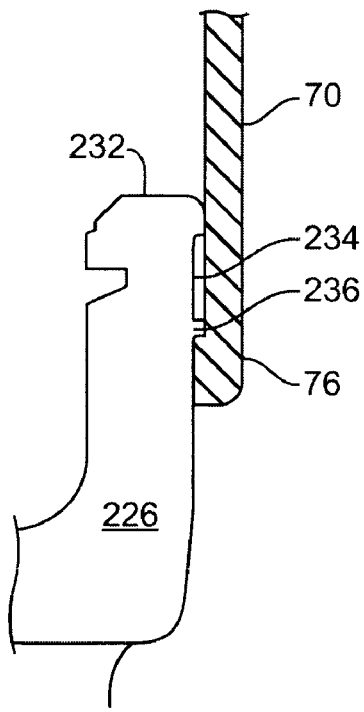
FIG. 24B is a side view of a seat with gripping fingers clamped below the lower flange of the seat according to the present invention.

Turning briefly now to FIG. 24A, there is shown the seat clamp fingers 70 pushing the nibs 76 of the seat clamp into corresponding recesses 234 formed in the outer surface of the seat 226. In another variation shown in FIG. 24B, the nibs 76 are clamped below a lower flange 236 to lock the seat 226 inside the seat receiving portion 58. In yet another variation shown in FIGS. 24C and 24D, the nibs 76 of the fingers 70 are clamped inside recesses as shown in FIG. 24C or below the lower flange 236 as shown in FIG. 24D. Additionally, in FIGS. 24C and 24D, a second portion 238 is configured to slide with respect to the fingers 70 and contact the upper surface 232 of the seat 226 to lock the seat 226 to the instrument 10.

Referring back to FIGS. 23A, 23B and 23C, the pin 204 pops into the pin hole 32 of the cannula 26 to lock the cannula assembly 12 into position and lock the seat 226 inside the cannula 26. The seat 226 is easily released from the cannula 26 by pulling on the knob 210. As a result of pulling the knob 210, the second spring 216 bias forces the seat clamp and the cannula 26 out from the distal end 80 of the locking shaft 14. If the seat 226 is not released, the resulting position of the instrument is as shown in FIG. 23C and an unlocked seat 226 is as shown in FIG. 23B.

Figure 25:
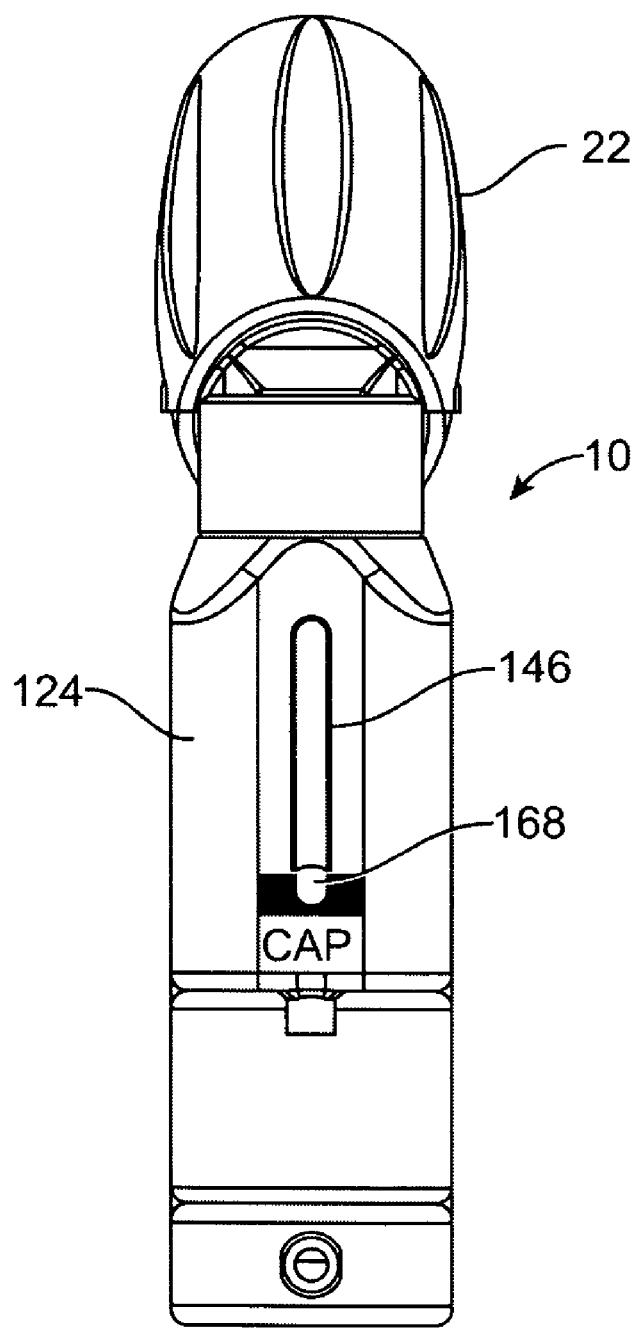
FIG. 25 is a partial top view showing the rack window and rack indicator according to the present invention.

From the position of the instrument 10 shown in FIG. 23C, the surgeon places the pinion driver 20 into the pinion bore 176 lining up the hexagonal shapes and inserting until the ball plunger 202 of the pinion driver 20 pops into the locking groove 180 of the pinion 170. It should be noted that the pinion driver 20 can be inserted on either side of the instrument, thereby, further increasing the ease of installation for the surgeon. The surgeon grabs the handle portion 198 and turns the pinion driver 20 to advance the rack 162 and connected plunger 16. The plunger 16 moves toward the distal end of the instrument 10 with respect to the body 124. With further advancement of the plunger 16, the rod engaging surfaces 108 contact the rod 230 and further advancement of the plunger 16 via the pinion driver 20 draws the rod 230 and bone screw system closer together until the rod 230 is substantially seated inside the rod channel 228. The degree of advancement of the plunger 16 is conveniently visible through the rack viewing window 146 in which the indicator 168 of the rack 162 is visible to the surgeon as shown in FIG. 25. The indicator 168 and window 146 advantageously provide a gauge for rod advancement. If the indicator 168 is all the way in a distal position as shown in FIG. 25, the rod 230 is fully seated. If the indicator 168 is not all the way in a distal position, the indicator 168 shows the surgeon how much more advancement of the plunger 16 is necessary to seat the rod 230. The surgeon is not required to look inside the patient to check to see if the rod is completely seated. Since sometimes the view inside the patient is obstructed by flesh and instruments, the instrument window and indicator facilitate installation for the surgeon and reduce overall installation time. If the rod 230 is not fully seated, the surgeon can continue to advance the pinion driver 20 and simply view the indicator 168 to see if seating is complete.

Figure 26:
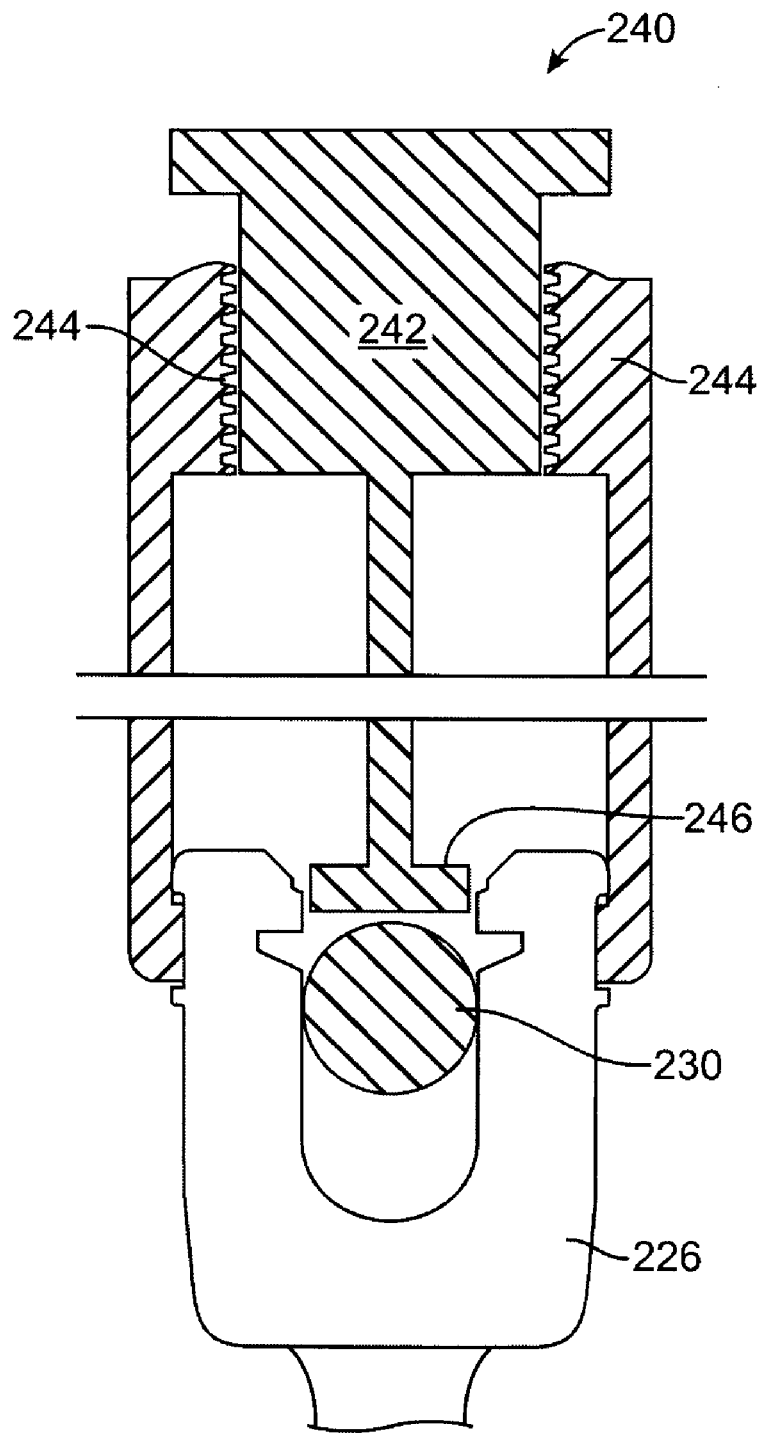
FIG. 26 is a partial view of a secondary reduction instrument connected to the seat according to the present invention.

Referring now to FIG. 26, after seating of the rod 230 is completed with the plunger, according to one variation of the invention, a secondary reduction instrument 240 is inserted into the proximal opening 151 of the bore 152. In one variation of the secondary reduction instrument 240, the secondary reduction instrument 240 includes a proximal threaded section 242 configured to engage a threaded bore section 244. The proximal threaded section 242 is connected to a distal piston section 246 configured to enter the seat 226 and rod channel 228 to push the rod 230 deeper into the seat by threaded advancement of the proximal threaded section 242. This variation highlights the utility and advantage of a configuration with a proximal opening 151 in the body 124 that connects with the bore 60 of the cannula 26 that provides access all the way to the bone screw system.

Figure 27A:
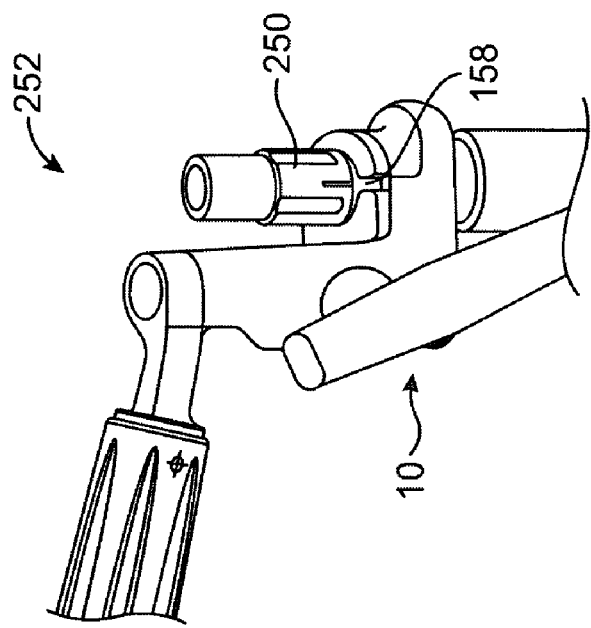
FIG. 27A is a partial view of the reduction instrument and locking mechanism inserter according to the present invention.
Figure 27B:
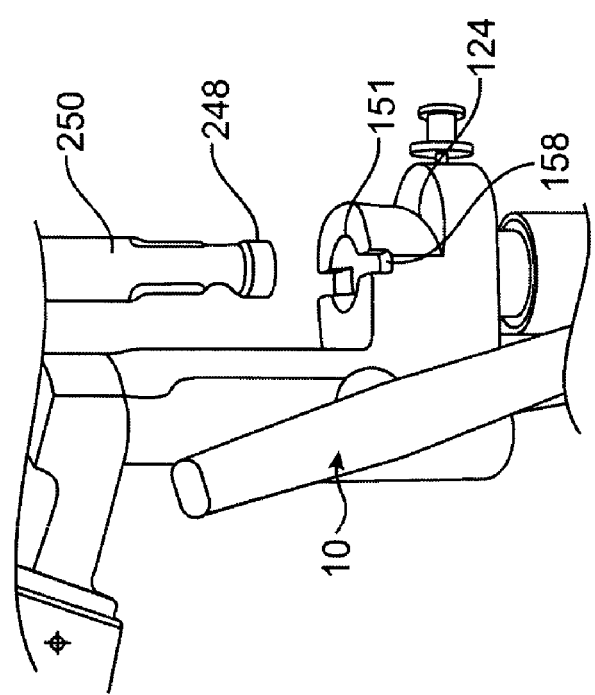
FIG. 27B is a partial view of the locking mechanism inserted into the bore of the rod reduction instrument according to the present invention.

Referring now to FIGS. 27A and 27B, after the rod is completely seated, a locking mechanism 248 in the form of a cap or set screw is inserted through the opening 151 in the bore 152 and located on the seat 226 to lock the rod 230 inside the rod channel. In one variation the locking mechanism 248 is in a form of a cap. The locking mechanism 248 is connected to a locking mechanism inserter instrument 250 which is inserted into the opening 151 of the bore 152 of the body 124 as shown in FIG. 27A. The locking mechanism inserter notches 158 orientate the locking mechanism inserter instrument 250 with respect to the rod reducer 10. Once the locking mechanism 248 is delivered and inserted into the seat 226, the locking mechanism inserter instrument 250 is turned clockwise, for example, to lock the locking mechanism to the seat 226. A second portion 252 of the locking mechanism inserter instrument 250 is turned to release the locking mechanism 248 after which the inserter instrument 250 is removed from the bore 152 through opening 151.

Figure 28B:
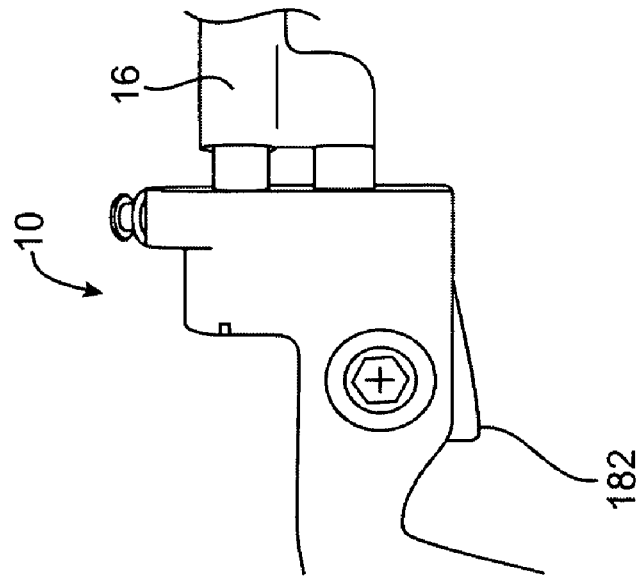
FIG. 28B is a partial view of the reduction instrument with the plunger in a retracted position according to the present invention.
Figure 28A:
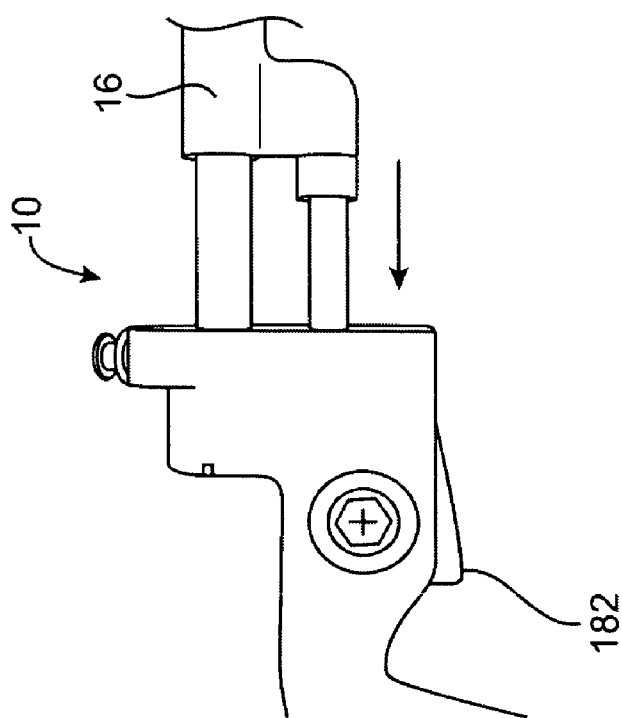
FIG. 28A is a partial view of the reduction instrument with the plunger in an advanced position according to the present invention.

Referring now to FIGS. 28A and 28B, the trigger 182 is pressed to pivot the rack engaging end 184 away from the rack 162 to retract the plunger 16 via the spring force generated by the first spring 214. The pinion driver 20 is preferably removed prior to depressing the trigger 182 to avoid rapid de-rotation of the pinion driver 20 as the plunger 16 retracts to a position shown in FIG. 28B. The plunger 16 is advantageously retracted independent of the release of the seat 226 via pulling the knob 210 of the cannula spring lock system 128. While keeping the seat 226 locked to the rod reducer instrument 10, the retraction of the plunger 16 permits the adjustment of the vertebral body via leverage placed on the handle 22 and then followed by another advancement of the plunger to seat the rod via the plunger driver 126. This process can be repeated to help seat the rod into position in difficult anatomical situations.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A rod reduction instrument for positioning a rod relative to a seat of a bone anchor in a spinal implant system, comprising:
a body having a handle at a proximal end of the instrument;
an inner cannula having a first proximal end, a first distal end configured to receive a seat and a first longitudinal axis defining a first bore from the first proximal end to the first distal end; the inner cannula being connected to the body at the first proximal end such that it is movable with respect to the body; the inner cannula having a first rod channel opening at the first distal end and extending towards the first proximal end; the inner cannula having a seat clamp at the first distal end configured to lock the inner cannula to the seat of a bone anchor; the seat clamp having at least one deflectable member;

a middle cannula having a second proximal end, a second distal end and a second longitudinal axis defining a second bore from the second proximal end to the second distal end; the middle cannula being connected to the body at the second proximal end; the middle cannula being positioned at least partially over the inner cannula and movable with respect to the inner cannula; the middle cannula having a second rod channel opening at the second distal end and extending towards the second proximal end; the second rod channel being substantially aligned with the first rod channel;

an outer cannula having a third proximal end, a third distal end and a third longitudinal axis defining a third bore from the third proximal end to the third distal end; the outer cannula being positioned at least partially over the middle cannula and movable with respect to the middle cannula; the outer cannula having a third rod channel opening at the third distal end and extending towards the third proximal end; the third rod channel being substantially aligned with the first and second rod channels;

wherein the instrument is configured to receive the seat of a bone anchor at the first distal end and configured to lock to the seat at the first distal end with movement of the instrument in a direction towards the seat such that such movement slides the middle cannula distally with respect to the inner cannula and over the at least one deflectable member to thereby deflect the at least one deflectable member inwardly towards the first longitudinal axis and lock the at least one deflectable member to the seat; and wherein movement of the middle cannula proximally with respect to the inner cannula uncovers the at least one deflectable member allowing the deflectable member to spring away from the seat and the first longitudinal axis to thereby unlock the seat from the instrument;

wherein, with the rod to be reduced located in one of the first or second rod channels and the seat received in the first distal end of the inner cannula, movement of the outer cannula distally with respect to the middle cannula slides the outer cannula over the middle cannula to engage the third rod channel with the rod and reduce the distance between the rod and the seat.

2. The rod reduction instrument of claim 1 further including a first spring disposed between the inner cannula and middle cannula to bias the inner cannula distally relative to the middle cannula.

3. The rod reduction instrument of claim 1 further including a first locking pin configured to releasably lock the inner cannula relative to the middle cannula such that the seat is locked to the rod reduction instrument when the first locking pin is locked and the seat is unlocked when the first locking pin is released.

4. The rod reduction instrument of claim 1 further including a second spring disposed between the middle cannula and the outer cannula to bias the outer cannula proximally relative to the middle cannula.

5. The rod reduction instrument of claim 1 further including a second locking pin configured to releasably lock the outer cannula relative to the middle cannula.

6. The rod reduction instrument of claim 1 further including a driver configured to translate the outer cannula.

7. The rod reduction instrument of claim 6 wherein the driver is configured with a removable handle insertable on either side of the instrument to drive the driver.

8. The rod reduction instrument of claim 1 further including:
   a first locking pin configured to releasably lock the inner cannula relative to the middle cannula such that the seat is locked to the rod reduction instrument when the first locking pin is locked and the seat is unlocked when the first locking pin is released
   a second locking pin configured to releasably lock the outer cannula relative to the middle cannula;
   wherein the first and second locking pins are independently activatable.

9. The rod reduction instrument of claim 1 further including an indicator connected to the outer cannula indicating the degree of advancement of the outer cannula relative to the seat.

10. A rod reduction system for positioning a rod relative to a seat of a bone anchor of a spinal implant system, comprising:
   an inner cannula, comprising:
      a first longitudinal axis;
      a first proximal end portion;
      a first distal end portion, comprising:
         a first rod receiving opening; and
         a seat clamp configured to couple the distal end of the inner cannula to the seat of the bone anchor during use, wherein the seat clamp comprises an outwardly biased deflectable member that is configured to be deflected inward toward the first longitudinal axis to engage at least a portion of the bone anchor during use to couple the distal end portion of the inner cannula to the seat of the bone anchor; and
      a first internal bore extending longitudinally along a length of the inner cannula;
   a middle cannula, comprising:
      a second longitudinal axis configured to be substantially aligned with the first longitudinal axis of the inner cannula during use;
      a second proximal end portion;
      a second distal end portion comprising a second rod receiving opening; and
      a second internal bore extending longitudinally along a length of the middle cannula;
      wherein the middle cannula is configured to be disposed at least partially over the inner cannula during use,
      wherein the second rod receiving opening is configured to be substantially aligned with the first rod receiving opening of the inner cannula during use, and
      wherein the middle cannula is configured to slide longitudinally in a distal direction with respect to the inner cannula to deflect the deflectable member inward toward the first longitudinal axis to engage at least a portion of the bone anchor during use such that sliding of the middle cannula in the distal direction results in coupling of the distal end portion of the inner cannula to the seat of the bone anchor; and
   an outer cannula, comprising:
      a third longitudinal axis configured to be substantially aligned with the first and second longitudinal axes of the inner and middle cannulas during use;
      a third proximal end portion;

a third distal end portion comprising a third rod receiving opening configured to engage the rod during use to draw the rod at least partially toward the seat of the bone anchor such that a distance between the rod and the seat is reduced; and a third internal bore extending longitudinally along a length of the outer cannula;

wherein the outer cannula is configured to be disposed at least partially over the middle cannula, wherein the third rod receiving opening is substantially aligned with the first and second rod receiving openings of the inner and middle cannulas, and wherein the outer cannula is configured to slide longitudinally in a distal direction with respect to the middle cannula, and wherein sliding of the outer cannula longitudinally in the distal direction is configured to result in the third rod receiving opening engaging the rod during use to draw the rod at least partially toward the seat of the bone anchor such that the distance between the rod and the seat is reduced.

11. The system of claim 10, wherein the middle cannula is configured to slide longitudinally in a proximal direction with respect to the inner cannula to enable the deflectable member to extend outward away from the first longitudinal axis to disengage at least a portion of the bone anchor during use such that sliding of the middle cannula in the proximal direction allows for de-coupling of the distal end of the inner cannula from the seat of the bone anchor.

12. A rod reduction system for positioning a rod relative to a seat of a bone anchor of a spinal implant system, comprising:

an inner cannula, comprising:
  a first longitudinal axis;
  a first proximal end portion;
  a first distal end portion comprising:
    a first rod receiving recess; and
    a seat clamp configured to couple the distal end of the inner cannula to the seat of the bone anchor, wherein the seat clamp comprises a locking member that is configured to be deflected inward toward the first longitudinal axis to engage at least a portion of the bone anchor during use to couple the inner cannula to the seat of the bone anchor; and
  a first internal bore extending in a longitudinally along a length of the inner cannula;

a middle cannula, comprising:
  a second proximal end portion;
  a second distal end portion comprising a second rod receiving recess; and
  a second internal bore extending longitudinally along a length of the middle cannula;
  wherein the middle cannula is configured to be disposed at least partially over the inner cannula during use,
  wherein the second rod receiving recess is configured to be substantially aligned with the first rod receiving recess of the inner cannula during use, and
  wherein the middle cannula is configured to slide longitudinally in a distal direction with respect to the inner cannula to deflect the locking member inward toward the first longitudinal axis to engage at least a portion of the bone anchor during use such that sliding of the middle cannula in the distal direction results in coupling of the inner cannula to the seat of the bone anchor; and an outer cannula, comprising:
  a third proximal end portion;
  a third distal end portion comprising a third rod receiving recess configured to engage the rod during use to urge the rod at least partially toward the seat of the bone anchor during use; and
  a third internal bore extending longitudinally along a length of the outer cannula;
  wherein the outer cannula is configured to be disposed at least partially over the middle cannula,
  wherein the third rod receiving recess is substantially aligned with the first and second rod receiving recesses of the inner and middle cannulas,
  wherein the outer cannula is configured to slide longitudinally in a distal direction with respect to the middle cannula, and
  wherein sliding of the outer cannula longitudinally in the distal direction is configured to result in the third rod receiving recess engaging the rod during use to urge the rod at least partially toward the seat of the bone anchor.

13. The system of claim 12, wherein the middle cannula is configured to slide longitudinally in a proximal direction with respect to the inner cannula to enable the locking member to deflect outward to disengage at least a portion of the bone anchor during use, such that sliding of the middle cannula in the proximal direction allows for de-coupling of the inner cannula from the seat of the bone anchor.

14. A rod reduction system for positioning a rod relative to a seat of a bone anchor of a spinal implant system, comprising:

an inner cannula, comprising:
  a first distal end portion comprising:
    a first rod receiving recess; and
    an actuatable seat clamp configured to couple to the bone anchor during use; and a middle cannula, comprising:
  a second distal end portion comprising a second rod receiving recess; and
  wherein the middle cannula is configured to be disposed at least partially over the inner cannula during use,
  wherein the second rod receiving recess is configured to be substantially aligned with the first rod receiving recess of the inner cannula during use, and
  wherein the middle cannula is configured to slide in a distal direction with respect to the inner cannula during use to actuate the seat clamp to couple to the bone anchor; and an outer cannula, comprising:
  a third distal end portion comprising a distal end portion configured to engage the rod during use to urge the rod at least partially toward the seat of the bone anchor during use,
  wherein the outer cannula is configured to be disposed at least partially over the middle cannula,
  wherein the outer cannula is configured to slide longitudinally in a distal direction with respect to the middle cannula, and
  wherein sliding of the outer cannula longitudinally in the distal direction is configured to result in the distal end portion engaging the rod during use to urge the rod at least partially toward the seat of the bone anchor.

15. The system of claim 14, wherein the middle cannula is configured to slide in a proximal direction with respect to the inner cannula during use to enable the seat clamp to de-couple from the bone anchor.

16. A rod reduction system for positioning a rod relative to a seat of a bone anchor of a spinal implant system, comprising:

a first cannula, comprising:
  a first longitudinal axis;
  a first proximal end portion;
  a first distal end portion comprising:
    a first rod receiving opening; and
    a seat clamp configured to couple the distal end of the first cannula to the seat of the bone anchor, wherein the seat clamp comprises an outwardly biased deflectable member that is configured to be deflected inward toward the first longitudinal axis to engage at least a portion of the bone anchor during use to couple the distal end portion of the first cannula to the seat of the bone anchor; and
  a first internal bore extending in a longitudinally along a length of the first cannula;
a second cannula, comprising:
  a second longitudinal axis configured to be substantially aligned with the first longitudinal axis of the first cannula during use;
  a second proximal end portion;
  a second distal end portion comprising a second rod receiving opening; and
  a second internal bore extending longitudinally along a length of the second cannula;
  wherein the second cannula is configured to be disposed at least partially over the first cannula during use,
  wherein the second rod receiving opening is configured to be substantially aligned with the first rod receiving opening of the first cannula during use, and
  wherein the second cannula is configured to slide longitudinally in a distal direction with respect to the first cannula to deflect the deflectable member inward toward the first longitudinal axis to engage at least a portion of the bone anchor during use such that sliding of the second cannula in the distal direction results in coupling of the distal end portion of the first cannula to the seat of the bone anchor; and
a third cannula, comprising:
  a third longitudinal axis configured to be substantially aligned with the first and second longitudinal axes of the first and second cannulas during use;
  a third proximal end portion;
  a third distal end portion comprising a third rod receiving opening configured to engage the rod during use to draw the rod at least partially toward the seat of the bone anchor during use such that a distance between the rod and the seat is reduced; and
  a third internal bore extending longitudinally along a length of the third cannula;
  wherein the third cannula is configured to be disposed at least partially over the second cannula,
  wherein the third rod receiving opening is substantially aligned with the first and second rod receiving openings of the first and second cannulas, and
  wherein the third cannula is configured to slide longitudinally in a distal direction with respect to the second cannula, and
  wherein sliding of the third cannula longitudinally in the distal direction is configured to result in the third rod receiving opening engaging the rod during use to draw the rod at least partially toward the seat of the bone anchor such that the distance between the rod and the seat is reduced.

17. The system of claim 16, wherein the second cannula is configured to slide longitudinally in a proximal direction with respect to the first cannula to enable the deflectable member to extend outward away from the first longitudinal axis to disengage at least a portion of the bone anchor during use such that sliding of the second cannula in the proximal direction allows for de-coupling of the distal end of the first cannula from the seat of the bone anchor.

18. A rod reduction system for positioning a rod relative to a seat of a bone anchor of a spinal implant system, comprising:
a first cannula, comprising:
  a first longitudinal axis;
  a first proximal end portion;
  a first distal end portion comprising:
    a first rod receiving recess; and
    a seat clamp configured to couple the distal end of the first cannula to the seat of the bone anchor, wherein the seat clamp comprises a locking member that is configured to be deflected inward toward the first longitudinal axis to engage at least a portion of the bone anchor during use to couple the first cannula to the seat of the bone anchor; and
  a first internal bore extending in a longitudinally along a length of the first cannula;
a second cannula, comprising:
  a second proximal end portion;
  a second distal end portion comprising a second rod receiving recess; and
  a second internal bore extending longitudinally along a length of the second cannula;
  wherein the second rod receiving recess is configured to be substantially aligned with the first rod receiving recess of the first cannula during use, and
  wherein the second cannula is configured to slide longitudinally in a distal direction with respect to the first cannula to deflect the locking member inward toward the first longitudinal axis to engage at least a portion of the bone anchor during use such that sliding of the second cannula in the distal direction results in coupling of the first cannula to the seat of the bone anchor; and
a third cannula, comprising:
  a third proximal end portion;
  a third distal end portion comprising a third rod receiving recess configured to engage the rod during use to urge the rod at least partially toward the seat of the bone anchor during use; and
  a third internal bore extending longitudinally along a length of the third cannula;
  wherein the third rod receiving recess is substantially aligned with the first and second rod receiving recesses of the first and second cannulas,
  wherein the third cannula is configured to slide longitudinally in a distal direction with respect to the second cannula, and
  wherein sliding of the third cannula longitudinally in the distal direction is configured to result in the third rod receiving recess engaging the rod during use to urge the rod at least partially toward the seat of the bone anchor.

19. The system of claim 18, wherein the first cannula, second cannula and third cannula are disposed substantially concentrically with respect to one another.

20. The system of claim 18, wherein the second cannula is configured to be disposed at least partially over the first cannula during use, and wherein the third cannula is configured to be disposed at least partially over the second cannula during use.

21. The system of claim 18, wherein the second cannula is configured to slide longitudinally in a proximal direction with respect to the first cannula to enable the locking member deflect outward to disengage at least a portion of the bone anchor during use such that sliding of the second cannula in the proximal direction allows for de-coupling of the first cannula from the seat of the bone anchor.

22. A rod reduction system for positioning a rod relative to a seat of a bone anchor of a spinal implant system, comprising:
- a first cannula, comprising:
  - a first distal end portion comprising:
    - a first rod receiving recess; and
    - an actuatable seat clamp configured to couple to the bone anchor during use; and
- a second cannula, comprising:
  - a second distal end portion comprising a second rod receiving recess; and
  - wherein the second rod receiving recess is configured to be substantially aligned with the first rod receiving recess of the inner cannula during use, and
  - wherein the second cannula is configured to slide in a distal direction with respect to the first cannula during use to actuate the seat clamp to couple to the bone anchor; and
- a third cannula, comprising:
  - a third distal end portion comprising a distal end portion configured to engage the rod during use to urge the rod at least partially toward the seat of the bone anchor during use,
  - wherein the third cannula is configured to slide longitudinally in a distal direction with respect to the second cannula, and
  - wherein sliding of the third cannula longitudinally in the distal direction is configured to result in the distal end portion engaging the rod during use to urge the rod at least partially toward the seat of the bone anchor.

23. The system of claim 22, wherein the first cannula, second cannula and third cannula are disposed substantially concentrically with respect to one another.

24. The system of claim 22, wherein the second cannula is configured to be disposed at least partially over the first cannula during use, and wherein the third cannula is configured to be disposed at least partially over the second cannula during use.

25. The system of claim 22, wherein the middle cannula is configured to slide in a proximal direction with respect to the inner cannula during use to enable the seat clamp to de-couple from the bone anchor.

* * * * *